US012746362B2

(12) United States Patent
Dantanarayana

(10) Patent No.: US 12,746,362 B2
(45) Date of Patent: Sep. 29, 2026

(54) VARIABLE FLOW VENT ASSEMBLY FOR A CONDUIT MASK

(71) Applicant: RESMED PTY LTD, Bella Vista (AU)

(72) Inventor: Muditha Pradeep Dantanarayana, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 784 days.

(21) Appl. No.: 18/028,711

(22) PCT Filed: Aug. 27, 2021

(86) PCT No.: PCT/AU2021/050988
§ 371 (c)(1),
(2) Date: Mar. 27, 2023

(87) PCT Pub. No.: WO2022/067374
PCT Pub. Date: Apr. 7, 2022

(65) Prior Publication Data

US 2023/0364375 A1 Nov. 16, 2023

(30) Foreign Application Priority Data

Sep. 30, 2020 (AU) ................................ 2020903522

(51) Int. Cl.
*A61M 16/20* (2006.01)
*A61M 16/06* (2006.01)
(Continued)

(52) U.S. Cl.
CPC ...... *A61M 16/208* (2013.01); *A61M 16/0616* (2014.02); *A61M 16/0683* (2013.01); *A61M 16/0875* (2013.01); *F16K 15/16* (2013.01)

(58) Field of Classification Search
CPC ............ A61M 16/208; A61M 16/0616; A61M 16/0683; A61M 16/0875; A61M 16/0075;
(Continued)

(56) References Cited

U.S. PATENT DOCUMENTS

| | | | |
|---|---|---|---|
| 4,782,832 | A | 11/1988 | Trimble et al. |
| 4,944,310 | A | 7/1990 | Sullivan |

(Continued)

FOREIGN PATENT DOCUMENTS

| | | | |
|---|---|---|---|
| WO | WO 98/004310 | A1 | 2/1998 |
| WO | WO 98/034665 | A1 | 8/1998 |

(Continued)

OTHER PUBLICATIONS

"*Respiratory Physiology*", by John B. West, Lippincott Williams & Wilkins, 9th edition published 2012 (8 pages).

(Continued)

*Primary Examiner* — Victoria Murphy
(74) *Attorney, Agent, or Firm* — Nixon & Vanderhye P.C.

(57) ABSTRACT

The technology relates to a variable flow vent assembly for a conduit mask configured to deliver a flow of breathable gas at a positive pressure to an airway entrance of a patient and allow a flow of exhaled gas from the airway of the patient to exit the vent assembly to ambient. The variable flow vent assembly is further configured to include a valve, wherein the valve is arranged to allow for the regulation of the flow of breathable gas to the patient and the regulation of the vent flow rate of exhaled gas leaving the vent assembly to ambient. By changing certain characteristics of the valve and by tuning the valve through variants in design, the resultant vent flow rate for a given air pressure can be altered in order to obtain the best treatment outcome for the patients individual requirements.

28 Claims, 20 Drawing Sheets

(51) Int. Cl.
*A61M 16/08* (2006.01)
*F16K 15/16* (2006.01)

(58) Field of Classification Search
CPC .......... A61M 16/0622; A61M 16/0633; A61M 16/0666; A61M 16/0688; A61M 16/0858; A61M 16/0883; A61M 16/107; A61M 16/1085; A61M 16/109; A61M 16/1095; A61M 16/205; A61M 2202/0225; A61M 16/0833; A61M 16/0066; A61M 16/12; A61M 2016/0015; A61M 2016/0027; A61M 2016/003; A61M 2202/0208; A61M 2205/3331; A61M 2205/3334; A61M 2205/3653; A61M 2205/42; A61M 2205/502; A61M 2205/8206; A61M 2209/088; A61M 16/16; A61M 16/024; A61M 16/06; A61M 16/20; A61M 16/0816; F16K 15/16; F16K 7/18
See application file for complete search history.

(56) References Cited

U.S. PATENT DOCUMENTS

| | | | | |
|---|---|---|---|---|
| 5,687,715 | A | 11/1997 | Landis | |
| 6,478,026 | B1 | 11/2002 | Wood | |
| 6,532,959 | B1 | 3/2003 | Berthon-Jones | |
| 6,581,594 | B1 | 6/2003 | Drew et al. | |
| 7,191,781 | B2 | 3/2007 | Wood | |
| 7,866,944 | B2 | 1/2011 | Kenyon et al. | |
| 8,636,479 | B2 | 1/2014 | Kenyon et al. | |
| 8,638,014 | B2 | 1/2014 | Sears et al. | |
| 8,733,349 | B2 | 5/2014 | Bath et al. | |
| 2002/0092527 | A1 | 7/2002 | Wood | |
| 2003/0116163 | A1* | 6/2003 | Wood | A61M 16/0666 128/207.18 |
| 2004/0255948 | A1 | 12/2004 | Smith et al. | |
| 2009/0044808 | A1 | 2/2009 | Guney et al. | |
| 2009/0050156 | A1 | 2/2009 | Ng et al. | |
| 2010/0000534 | A1 | 1/2010 | Kooij et al. | |
| 2012/0325211 | A1* | 12/2012 | Allum | A61M 16/0605 128/205.24 |
| 2016/0220780 | A1 | 8/2016 | Nitta | |
| 2017/0312465 | A1* | 11/2017 | Kwok | A61M 16/0616 |
| 2019/0209804 | A1 | 7/2019 | Dantanarayana et al. | |
| 2019/0388645 | A1 | 12/2019 | Chodkowski et al. | |
| 2020/0269001 | A1 | 8/2020 | Guney et al. | |

FOREIGN PATENT DOCUMENTS

| | | | | |
|---|---|---|---|---|
| WO | WO 00/38772 | A1 | 7/2000 | |
| WO | WO 00/78381 | A1 | 12/2000 | |
| WO | WO 02/051486 | A1 | 7/2002 | |
| WO | WO 2004/073778 | A1 | 9/2004 | |
| WO | WO 2005/063328 | A1 | 7/2005 | |
| WO | WO 2006/074513 | A1 | 7/2006 | |
| WO | WO 2006/130903 | A1 | 12/2006 | |
| WO | WO 2009/052560 | A1 | 4/2009 | |
| WO | WO 2010/135785 | A1 | 12/2010 | |
| WO | WO 2010/141983 | A1 | 12/2010 | |
| WO | WO 2012/171072 | A1 | 12/2012 | |
| WO | WO 2013/020167 | A1 | 2/2013 | |
| WO | WO 2013/040198 | A2 | 3/2013 | |
| WO | WO-2014129913 | A1 * | 8/2014 | A61M 16/06 |
| WO | WO 2020/170207 | A1 | 8/2020 | |

OTHER PUBLICATIONS

International Preliminary Report on Patentability dated Jan. 6, 2023 issued in International Application No. PCT/AU2021/050988 (22 pages).
International Search Report dated Nov. 24, 2021 issued in International Application No. PCT/AU2021/050988 (8 pages).
Written Opinion of the International Searching Authority dated Nov. 24, 2021 issued in International Application No. PCT/AU2021/050988 (7 pages).
Written Opinion of the International Preliminary Examining Authority dated Mar. 22, 2022 issued in International Application No. PCT/AU2021/050988 (5 pages).
Extended European Search Report mailed Sep. 17, 2024 in European Application No. 21873718.7, 8 pages.
Extended European Search Report mailed Feb. 13, 2025 in European Application No. 24218343.2, 8 pages.

* cited by examiner

VARIABLE FLOW VENT ASSEMBLY FOR A CONDUIT MASK

1 CROSS-REFERENCE TO RELATED APPLICATIONS

This application is the U.S. national phase of International Application No. PCT/AU2021/050988 filed Aug. 27, 2021 which designated the U.S. and claims priority to AU 2020903522 filed Sep. 30, 2020, the entire contents of each of which are hereby incorporated by reference.

2 BACKGROUND OF THE TECHNOLOGY

2.1 Field of the Technology

The present technology relates to one or more of the detection, diagnosis, treatment, prevention and amelioration of respiratory-related disorders. The present technology also relates to medical devices or apparatus, and their use.

2.2 Description of the Related Art

2.2.1 Human Respiratory System and Its Disorders

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "Respiratory Physiology", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Respiratory failure is an umbrella term for respiratory disorders in which the lungs are unable to inspire sufficient oxygen or exhale sufficient $CO_2$ to meet the patient's needs. Respiratory failure may encompass some or all of the following disorders.

A patient with respiratory insufficiency (a form of respiratory failure) may experience abnormal shortness of breath on exercise.

Obesity Hypoventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

2.2.2 Therapy

Various therapies, such as Continuous Positive Airway Pressure (CPAP) therapy, Non-invasive ventilation (NIV) and Invasive ventilation (IV) have been used to treat one or more of the above respiratory disorders.

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

2.2.2.1 Treatment Systems

These therapies may be provided by a treatment system or device. Such systems and devices may also be used to diagnose a condition without treating it.

A treatment system may comprise a Respiratory Pressure Therapy Device (RPT device), an air circuit, a humidifier, a patient interface, and data management.

Another form of treatment system is a mandibular repositioning device.

2.2.2.2 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 $cmH_2O$ relative to ambient pressure. For other forms of therapy, such as the delivery of oxygen, the patient interface may not include a seal sufficient to facilitate delivery to the airways of a supply of gas at a positive pressure of about 10 $cmH_2O$.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use, a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

2.2.2.2.1 Seal-Forming Structure

Patient interfaces may include a seal-forming structure. Since it is in direct contact with the patient's face, the shape and configuration of the seal-forming structure can have a direct impact the effectiveness and comfort of the patient interface.

A patient interface may be partly characterised according to the design intent of where the seal-forming structure is to engage with the face in use. In one form of patient interface, a seal-forming structure may comprise a first sub-portion to form a seal around the left naris and a second sub-portion to form a seal around the right naris. In one form of patient interface, a seal-forming structure may comprise a single element that surrounds both nares in use. Such single element may be designed to for example overlay an upper lip region and a nasal bridge region of a face. In one form of patient interface a seal-forming structure may comprise an element that surrounds a mouth region in use, e.g. by forming a seal on a lower lip region of a face. In one form of patient interface, a seal-forming structure may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming structure that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming structures may be designed for mass manufacture such that one design fit and be comfortable and effective for a wide range of different face shapes and sizes. To the extent to which there is a mismatch between the shape of the patient's face, and the seal-forming structure of the mass-manufactured patient interface, one or both must adapt in order for a seal to form.

One type of seal-forming structure extends around the periphery of the patient interface, and is intended to seal against the patient's face when force is applied to the patient interface with the seal-forming structure in confronting engagement with the patient's face. The seal-forming structure may include an air or fluid filled cushion, or a moulded or formed surface of a resilient seal element made of an elastomer such as a rubber. With this type of seal-forming structure, if the fit is not adequate, there will be gaps between the seal-forming structure and the face, and additional force will be required to force the patient interface against the face in order to achieve a seal.

Another type of seal-forming structure incorporates a flap seal of thin material positioned about the periphery of the mask so as to provide a self-sealing action against the face of the patient when positive pressure is applied within the mask. Like the previous style of seal forming portion, if the match between the face and the mask is not good, additional force may be required to achieve a seal, or the mask may leak. Furthermore, if the shape of the seal-forming structure does not match that of the patient, it may crease or buckle in use, giving rise to leaks.

Another type of seal-forming structure may comprise a friction-fit element, e.g. for insertion into a naris, however some patients find these uncomfortable.

Another form of seal-forming structure may use adhesive to achieve a seal. Some patients may find it inconvenient to constantly apply and remove an adhesive to their face.

A range of patient interface seal-forming structure technologies are disclosed in the following patent applications, assigned to ResMed Limited: WO 1998/004,310; WO 2006/074,513; WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT™ nasal pillows mask, SWIFT™ II nasal pillows mask, SWIFT™ LT nasal pillows mask, SWIFT™ FX nasal pillows mask and MIRAGE LIBERTY™ full-face mask. The following patent applications, assigned to ResMed Limited, describe examples of nasal pillows masks: International Patent Application WO2004/073,778 (describing amongst other things aspects of the ResMed Limited SWIFT™ nasal pillows), US Patent Application 2009/0044808 (describing amongst other things aspects of the ResMed Limited SWIFT™ LT nasal pillows); International Patent Applications WO 2005/063,328 and WO 2006/130,903 (describing amongst other things aspects of the ResMed Limited MIRAGE LIBERTY™ full-face mask); International Patent Application WO 2009/052,560 (describing amongst other things aspects of the ResMed Limited SWIFT™ FX nasal pillows).

2.2.2.2.2 Positioning and Stabilising

A seal-forming structure of a patient interface used for positive air pressure therapy is subject to the corresponding force of the air pressure to disrupt a seal. Thus a variety of techniques have been used to position the seal-forming structure, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use.

2.2.2.2.3 Pressurised Air Conduit

In one type of treatment system, a flow of pressurised air is provided to a patient interface through a conduit in an air circuit that fluidly connects to the patient interface so that, when the patient interface is positioned on the patient's face during use, the conduit extends out of the patient interface forwards away from the patient's face. This may sometimes be referred to as an "elephant trunk" style of interface.

Some patients find such interfaces to be unsightly and are consequently deterred from wearing them, reducing patient compliance. Additionally, conduits connecting to an interface at the front of a patient's face may sometimes be vulnerable to becoming tangled up in bed clothes.

2.2.2.2.4 Pressurised Air Conduit used for Positioning/Stabilising the Seal-Forming Structure An alternative type of treatment system which seeks to address these problems comprises a patient interface in which a tube that delivers pressurised air to the patient's airways also functions as part of the headgear to position and stabilise the seal-forming portion of the patient interface to the appropriate part of the patient's face. This type of patient interface may be referred to as incorporating 'headgear tubing' or 'conduit headgear'. Such patient interfaces allow the conduit in the air circuit providing the flow of pressurised air from a respiratory pressure therapy device to connect to the patient interface in a position other than in front of the patient's face. One example of such a treatment system is disclosed in US Patent Publication No. 2007/0246043, the contents of which are incorporated herein by reference, in which the conduit connects to a tube in the patient interface through a port positioned in use on top of the patient's head.

2.2.2.3 Respiratory Pressure Therapy (RPT) Device

A respiratory pressure therapy (RPT) device may be used to deliver one or more of a number of therapies described above, such as by generating a flow of air for delivery to an entrance to the airways. The flow of air may be pressurised. Examples of RPT devices include a CPAP device and a ventilator.

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

2.2.2.4 Humidifier

Delivery of a flow of air without humidification may cause drying of airways. The use of a humidifier with an RPT device and the patient interface produces humidified gas that minimizes drying of the nasal mucosa and increases patient airway comfort. In addition, in cooler climates, warm air applied generally to the face area in and about the patient interface is more comfortable than cold air.

A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g. at a hospital). A medical humidifier for bedside placement may be small. A medical humidifier may be configured to only humidify and/or heat the flow of air delivered to the patient without humidifying and/or heating the patient's surroundings. Room-based systems (e.g. a sauna, an air conditioner, or an evaporative cooler), for example, may also humidify air that is breathed in by the patient, however those systems would also humidify and/or heat the entire room, which may cause discomfort to the occupants. Furthermore medical humidifiers may have more stringent safety constraints than industrial humidifiers While a number of medical humidifiers are known, they can suffer from one or more shortcomings. Some medical humidifiers may provide inadequate humidification, some are difficult or inconvenient to use by patients.

2.2.2.5 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient.

The vent may comprise an orifice and gas may flow through the orifice in use of the mask. Many such vents are noisy. Others may become blocked in use and thus provide insufficient washout. Some vents may be disruptive of the sleep of a bed partner 1100 of the patient 1000, e.g. through noise or focussed airflow.

ResMed Limited has developed a number of improved mask vent technologies. See International Patent Application Publication No. WO 1998/034,665; International Patent Application Publication No. WO 2000/078,381; U.S. Pat. No. 6,581,594; US Patent Application Publication No. US 2009/0050156; U.S. Pat. Application Publication No. 2009/0044808.

Table of noise of prior masks (ISO 17510-2:2007, 10 $cmH_2O$ pressure at 1 m)

| Mask name | Mask type | A-weighted sound power level dB(A) (uncertainty) | A-weighted sound pressure dB(A) (uncertainty) | Year (approx.) |
|---|---|---|---|---|
| Glue-on (*) | nasal | 50.9 | 42.9 | 1981 |
| ResCare standard (*) | nasal | 31.5 | 23.5 | 1993 |
| ResMed Mirage ™ (*) | nasal | 29.5 | 21.5 | 1998 |
| ResMed UltraMirage ™ | nasal | 36 (3) | 28 (3) | 2000 |
| ResMed Mirage Activa ™ | nasal | 32 (3) | 24 (3) | 2002 |
| ResMed Mirage Micro ™ | nasal | 30 (3) | 22 (3) | 2008 |
| ResMed Mirage ™ SoftGel | nasal | 29 (3) | 22 (3) | 2008 |
| ResMed Mirage ™ FX | nasal | 26 (3) | 18 (3) | 2010 |
| ResMed Mirage Swift ™ (*) | nasal pillows | 37 | 29 | 2004 |
| ResMed Mirage Swift ™ II | nasal pillows | 28 (3) | 20 (3) | 2005 |
| ResMed Mirage Swift ™ LT | nasal pillows | 25 (3) | 17 (3) | 2008 |
| ResMed AirFit P10 | nasal pillows | 21 (3) | 13 (3) | 2014 |

(*) one specimen only, measured using test method specified in ISO 3744 in CPAP mode at 10 $cmH_2O$)

Sound pressure values of a variety of objects are listed below.

| Object | A-weighted sound pressure dB(A) | Notes |
|---|---|---|
| Vacuum cleaner: Nilfisk Walter Broadly Litter Hog: B+ Grade | 68 | ISO 3744 at 1 m distance |
| Conversational speech | 60 | 1 m distance |
| Average home | 50 | |
| Quiet library | 40 | |
| Quiet bedroom at night | 30 | |
| Background in TV studio | 20 | |

3 BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

A first aspect of the present technology relates to apparatus used in the diagnosis, amelioration, treatment or prevention of a respiratory disorder.

Another aspect of the present technology relates to methods used in the diagnosis, amelioration, treatment or prevention of a respiratory disorder.

An aspect of certain forms of the present technology is to provide methods and/or apparatus that improve the compliance of patients with respiratory therapy.

One form of the present technology comprises a vent assembly for a patient interface for delivering a flow of breathable gas at a positive pressure to an airway entrance of a patient.

Another form of the present technology comprises a vent assembly for a patient interface for delivering a flow of breathable gas at a positive pressure to an airway entrance of a patient, wherein the vent assembly is configured for a patient interface comprising conduit headgear.

One aspect of the present technology relates to a vent assembly for a patient interface for delivering a flow of breathable gas at a positive pressure to an airway entrance of a patient. The vent assembly may comprise a vent body at least in part defining a vent chamber. The vent body may be configured to define a first inlet on a first side of the vent body, the first inlet being configured to receive a first inlet flow of breathable gas into the vent chamber. The vent body may further be configured to define a second inlet on a second side of the vent body, the second side being opposite the first side, the second inlet being configured to receive a second inlet flow of breathable gas into the vent chamber. The vent body may further be configured to define an opening configured to allow exit of the flow of breathable gas from the vent chamber for delivery to the airway entrance and to receive a flow of exhaled gas from the patient into the vent chamber. The vent body may further be configured to define a plurality of vent holes configured to allow a vent flow of exhaled gas from the vent chamber to ambient. The vent assembly may further comprise a valve configured to adopt a first configuration and a second configuration, wherein the valve at least partially blocks the plurality of vent holes by a different amount in the first configuration compared to the second configuration.

In examples: a) the valve may be configured to adopt a plurality of configurations between the first configuration and the second configuration, wherein the amount of blocking of the plurality of vent holes by the valve is different in each of the plurality of positions; b) the configuration adopted by the valve may be based on a pressure of gas in the vent chamber; c) the configuration adopted by the valve may be based on a breathing cycle of the patient in use; d) the configuration adopted by the valve when the patient exhales may be different from the configuration adopted by the valve when the patient inhales; and d) the valve may be configured to be biased to adopt the second configuration, wherein the amount of blocking of the plurality of vent holes by the valve is greater in the first configuration compared to the second configuration.

In further examples: a) the plurality of vent holes may comprise one or more active vent holes, wherein the vent assembly is configured so that the valve at least partially blocks the plurality of active vent holes by a different amount when the valve is in the first configuration compared to the second configuration; b) the plurality of vent holes may further comprise one or more passive vent holes, wherein the vent assembly is configured so that the amount of blocking of the passive vent holes by the valve is the same when the valve is in the first configuration as when the valve member is in the second configuration; and c) the vent assembly may be configured so that the passive vent holes are not blocked by the valve in the first configuration and are not blocked by the valve in the second configuration.

In further examples: a) the valve may comprise a first valve member and a second valve member, wherein each of the first valve member and the second valve member is configured to adopt a first position when the valve is in the first configuration and to adopt a second position when the valve is in the second configuration, wherein the respective valve member at least partially blocks a subset of the plurality of vent holes by a different amount in the first position compared to the second position; b) the first valve member may be positioned in a path of the first inlet flow of breathable gas from the first inlet and the second valve member may be positioned in a path of the second inlet flow of breathable gas from the second inlet; c) the first valve member may comprise a first membrane mounted to the vent body and the second valve member may comprise a second membrane mounted to the vent body; d) the first membrane and the second membrane may be pivotally mounted to the vent body; e) when each of the first and second valve members are in the first position, a surface of the respective membrane may abut against a respective seat portion of a first seat portion and a second seat portion of the vent body, wherein the plurality of vent holes are provided in the first and second seat portions; f) when each of the first and second valve members are in the first position, the respective membrane may lie on the respective seat portion over the respective subset of the plurality of vent holes to block the respective subset of the plurality of vent holes; g) a mounted edge of the first membrane may be pivotally mounted to the vent body at or proximate a part of the first seat portion proximal to the first inlet and the first membrane may extend from the mounted edge away from the first inlet, and wherein a mounted edge of the second membrane may be pivotally mounted to the vent body at or proximate a part of the second seat portion proximal to the second inlet and the second membrane may extend from the mounted edge away from the second inlet; h) the first seat portion and the second seat portion may be configured so that, when each of the first and second valve members are in the first position, a free end of the first and second valve members is spaced from the respective first and second seat portion to allow the flow of exhaled gas under the free ends of the first and second valve members; i) the first seat portion and the second seat portion may be substantially flat; j) the first seat portion and the second seat portion may be substantially convex; and k) the first seat portion may be oriented at an acute angle to the direction of the first inlet flow and the second seat portion may be oriented at an acute angle to the direction of the second inlet flow.

In a further example the vent assembly may be configured with the plurality of vent holes on an opposite side of the vent body to the opening.

In further examples: a) the one or more active vent holes may comprise a plurality of active vent holes and the plurality of active vent holes may be provided in the first and second seat portions, and the one or more passive vent holes may be provided in a wall of the vent body between the first and second seat portions; and b) the wall of the vent body in which the one or more passive vent holes are provided may be positioned directly opposite the opening.

In further examples: a) the vent assembly may be configured to provide a selected vent flow rate of exhaled gas from the vent chamber to ambient for a given pressure of breathable gas in the plenum chamber; and b) the vent assembly may be configured so that, in use, a vent flow rate of the flow of exhaled air from the vent chamber through the vent holes to ambient is substantially constant for a range of pressures inside the vent chamber.

In further examples: a) the vent assembly may further comprise a diffuser to diffuse the vent flow of exhaled gas from the vent chamber to ambient; b) the diffuser may comprise a diffuser member mounted to the vent body so that the diffuser member is positioned in the path of the vent flow of exhaled gas through the plurality of vent holes and so that a surface of the diffuser member facing the vent body is spaced apart from the vent body; and c) the diffuser may comprise a diffusing body positioned in a space between the vent body and the diffuser member.

Another aspect of the present technology relates to a patient interface for delivering a flow of breathable gas at a positive pressure to an airway entrance of a patient.

One form of the present technology relates to a patient interface for delivering a flow of breathable gas at a positive pressure to an airway entrance of a patient, the patient interface comprising a vent assembly, a plenum chamber, a seal-forming structure and a positioning and stabilising system.

In examples, the vent assembly may be a vent assembly according to any of the previously described aspects, forms and examples of the present technology.

In examples, the plenum chamber may be pressurisable to a therapeutic pressure of at least 4 $cmH_2O$ above ambient air pressure, the plenum chamber comprising the vent body of the vent assembly.

In examples, the seal-forming structure may be constructed and arranged to form a seal with a region of the patient's face surrounding the airway entrance. The seal-forming structure may have a hole therein such that the flow of breathable gas at said therapeutic pressure is delivered to the airway entrance. The seal-forming structure may be constructed and arranged to maintain said therapeutic pressure in the plenum chamber throughout the patient's respiratory cycle in use.

In examples, the positioning and stabilising structure may provide a force to hold the seal-forming structure in a therapeutically effective position on the patient's head. The positioning and stabilising structure may comprise at least two gas delivery tubes to receive the flow of breathable gas from a connection port configured to be positioned on top of the patient's head in use and to deliver the flow of breathable gas to the airway entrance via the plenum chamber. The gas delivery tubes may be constructed and arranged to contact, in use, at least a region of the patient's head superior to an otobasion superior of the patient's head. The gas delivery tubes may be constructed and arranged so that, in use, at least one of the gas delivery tubes is positioned in use on each side of the patient's head and extends across the respective cheek region. One of the gas delivery tubes may fluidly connect to the first inlet of the vent assembly and another of the gas delivery tubes may fluidly connect to the second inlet of the vent assembly. For example, the positioning and stabilising structure may be configured as conduit headgear.

Another aspect of the present technology relates to a vent assembly for a patient interface for delivering a flow of breathable gas at a positive pressure to an airway entrance of a patient. The vent assembly may comprise a vent body at least in part defining a vent chamber. The vent body may be configured to define an inlet to receive an inlet flow of breathable gas into the vent chamber. The vent body may be further configured to define an opening configured to allow exit of the flow of breathable gas from the vent chamber for delivery to the airway entrance and to receive a flow of exhaled gas from the patient into the vent chamber. The vent body may be further configured to define a plurality of vent holes configured to allow a vent flow of exhaled gas from the vent chamber to ambient. The vent assembly may further comprise a valve configured to adopt a first configuration and a second configuration, wherein the valve at least partially blocks the plurality of vent holes by a different amount in the first configuration compared to the second configuration. The valve may comprise a first valve member and a second valve member, wherein each of the first valve member and the second valve member is configured to adopt a first position when the valve is in the first configuration and to adopt a second position when the valve is in the second configuration, wherein the respective valve member at least partially blocks a subset of the plurality of vent holes by a different amount in the first position compared to the second position.

Another aspect of the present technology relates to a vent assembly for a patient interface for delivering a flow of breathable gas at a positive pressure to an airway entrance of a patient. The vent assembly may comprise a vent body at least in part defining a vent chamber. The vent body may be configured to define an inlet to receive an inlet flow of breathable gas into the vent chamber. The vent body may be further configured to define an opening configured to allow exit of the flow of breathable gas from the vent chamber for delivery to the airway entrance and to receive a flow of exhaled gas from the patient into the vent chamber. The vent body may be further configured to define a plurality of vent holes configured to allow a vent flow of exhaled gas from the vent chamber to ambient. The vent assembly may further comprise a valve configured to adopt a first configuration and a second configuration, wherein the valve at least partially blocks the plurality of vent holes by a different amount in the first configuration compared to the second configuration. The valve may comprise a valve member configured to adopt a first position when the valve is in the first configuration and to adopt a second position when the valve is in the second configuration, wherein the valve member at least partially blocks a subset of the plurality of vent holes by a different amount in the first position compared to the second position. When the valve member is in the first position, a part of the valve member may abut against a seat portion of the vent body, wherein the plurality of vent holes is provided in the seat portion. The seat portion may be configured so that, when the valve member is in the first position, a free end of the valve member is spaced from the seat portion to allow the flow of exhaled gas under a free end of the valve member.

Another aspect of the present technology relates to a vent assembly for a patient interface for delivering a flow of breathable gas at a positive pressure to an airway entrance of a patient. The vent assembly may comprise a vent body at least in part defining a vent chamber. The vent body may be configured to define an inlet to receive an inlet flow of breathable gas into the vent chamber. The vent body may be further configured to define an opening configured to allow exit of the flow of breathable gas from the vent chamber for delivery to the airway entrance and to receive a flow of exhaled gas from the patient into the vent chamber. The vent body may be further configured to define a plurality of vent holes configured to allow a vent flow of exhaled gas from the vent chamber to ambient. The vent assembly may further comprise a valve configured to adopt a first configuration and a second configuration, wherein the valve at least partially blocks the plurality of vent holes by a different amount in the first configuration compared to the second configuration. The valve may comprise a valve member configured to adopt a first position when the valve is in the first configuration and to adopt a second position when the valve is in the second configuration, wherein the valve member at least partially blocks a subset of the plurality of vent holes by a different amount in the first position compared to the second position. When the valve member is in the first position, a part of the valve member may abut against a seat portion of the vent body, wherein the plurality of vent holes is provided in the seat portion. The seat portion may be oriented at an acute angle to the direction of the inlet flow.

An aspect of one form of the present technology is a method of manufacturing apparatus.

An aspect of certain forms of the present technology is a medical device that is easy to use, e.g. by a person who does not have medical training, by a person who has limited dexterity, vision or by a person with limited experience in using this type of medical device.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Treatment Systems

FIG. 1A shows a system including a patient 1000 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown. The patient is sleeping in a supine sleeping position.

4.2 Respiratory System and Facial Anatomy

FIG. 2A shows an overview of a human respiratory system including the nasal and oral cavities, the larynx, vocal folds, oesophagus, trachea, bronchus, lung, alveolar sacs, heart and diaphragm.

4.3 Patient Interface

FIG. 3A shows a patient interface in the form of a nasal mask in accordance with one form of the present technology.

4.4 RPT Device

4.5 Humidifier

Figure 5A:
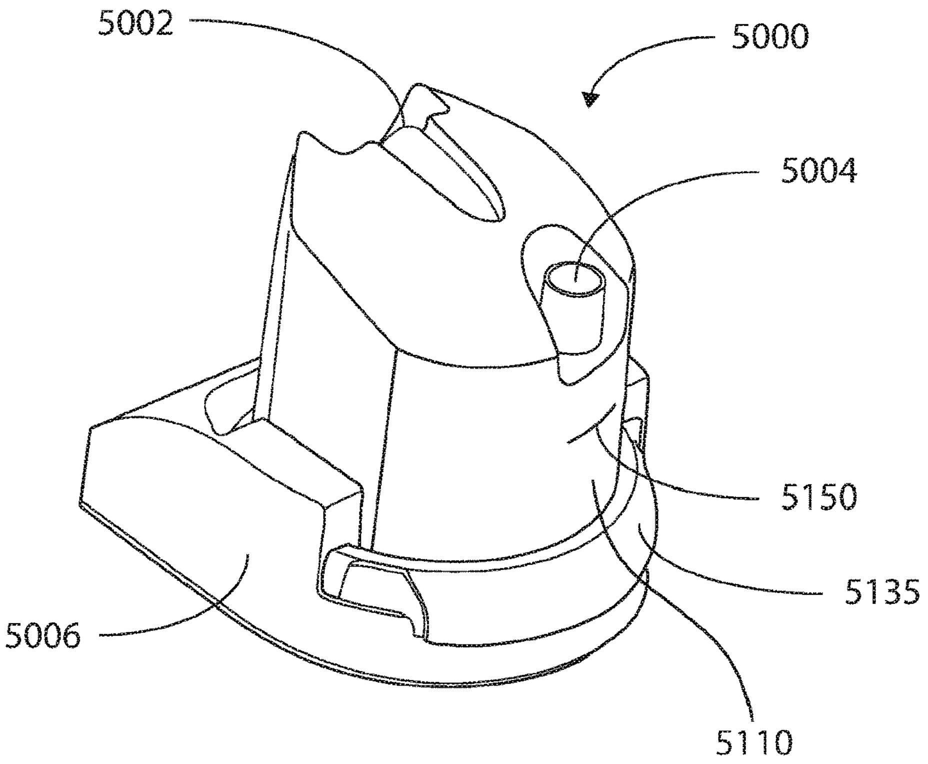

FIG. 5A shows an isometric view of a humidifier in accordance with one form of the present technology.

Figure 5B:
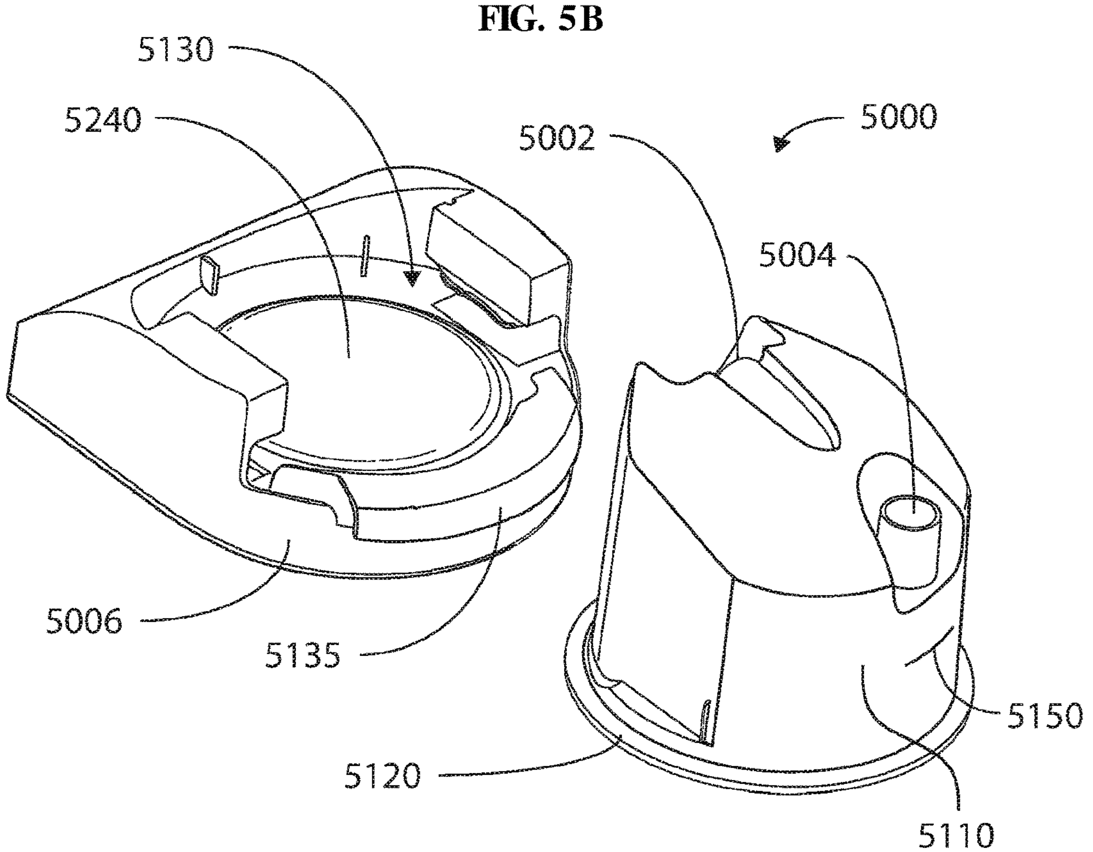

FIG. 5B shows an isometric view of a humidifier in accordance with one form of the present technology, showing a humidifier reservoir 5110 removed from the humidifier reservoir dock 5130.

4.6 Breathing Waveforms

Figure 6A:
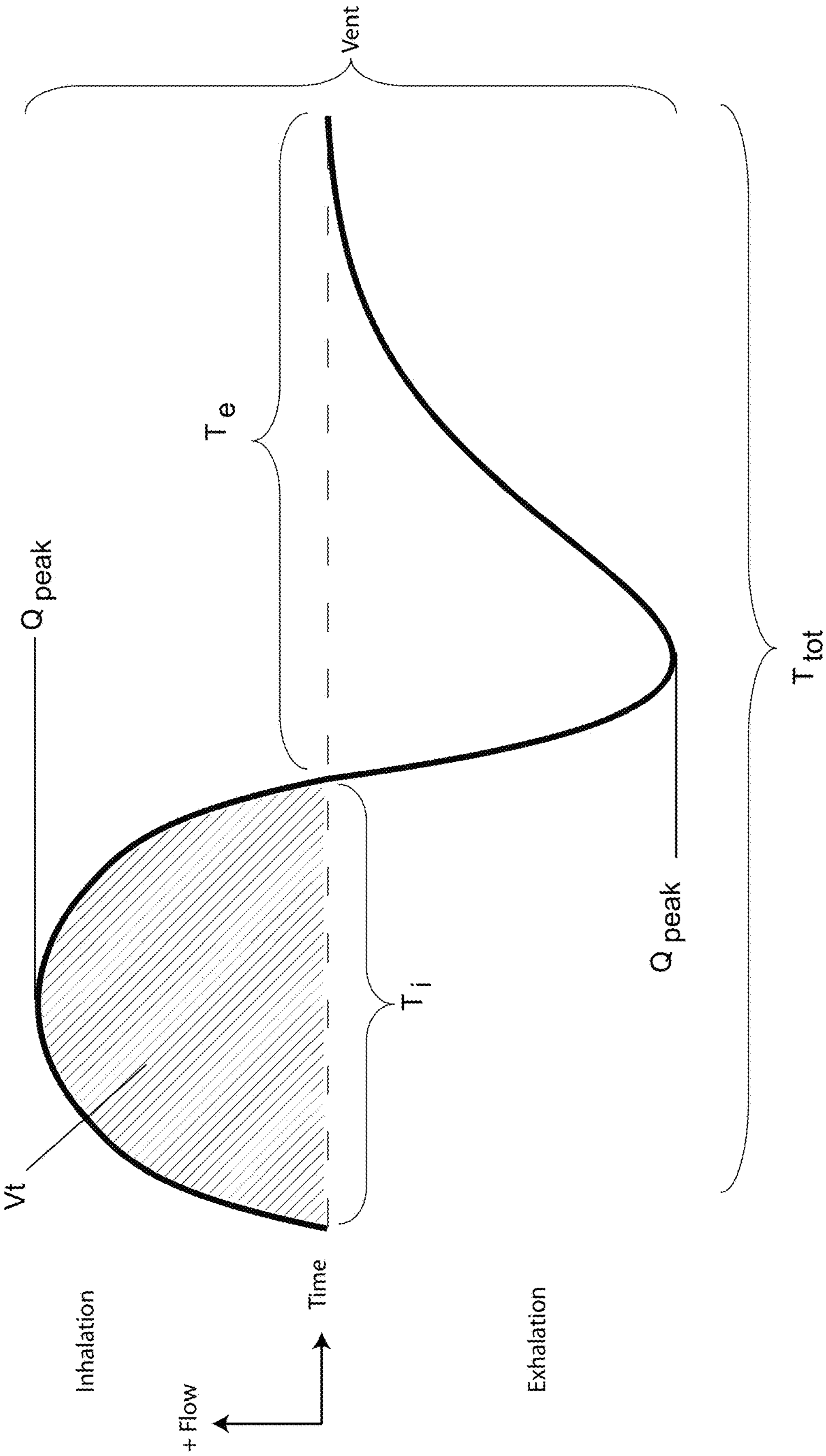

FIG. 6A shows a model typical breath waveform of a person while sleeping.

4.7 Conduit Headgear

Figure 7A:
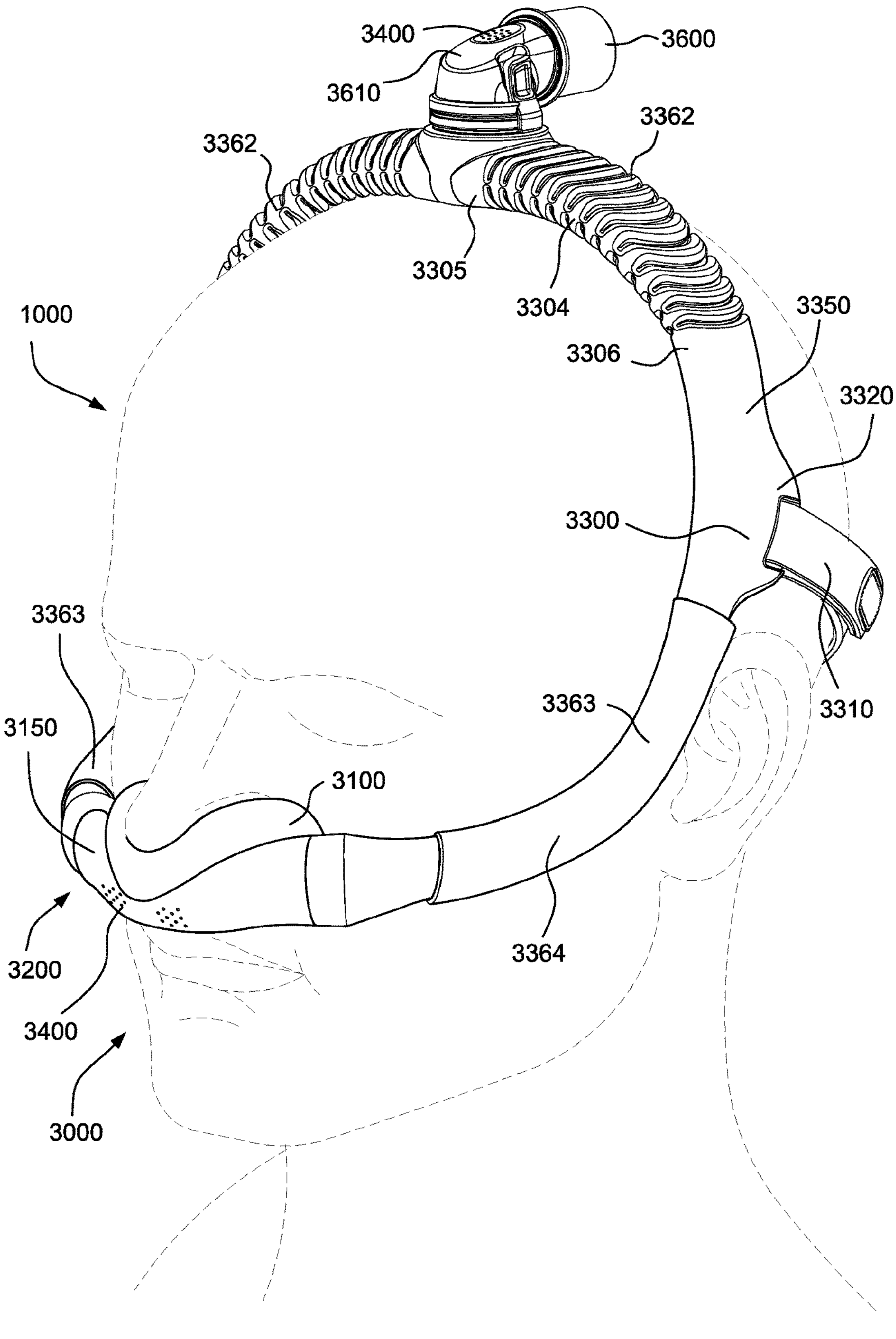

FIG. 7A shows a patient interface 3000 in the form of conduit headgear including a patient 1000 wearing the conduit headgear.

Figure 7B:
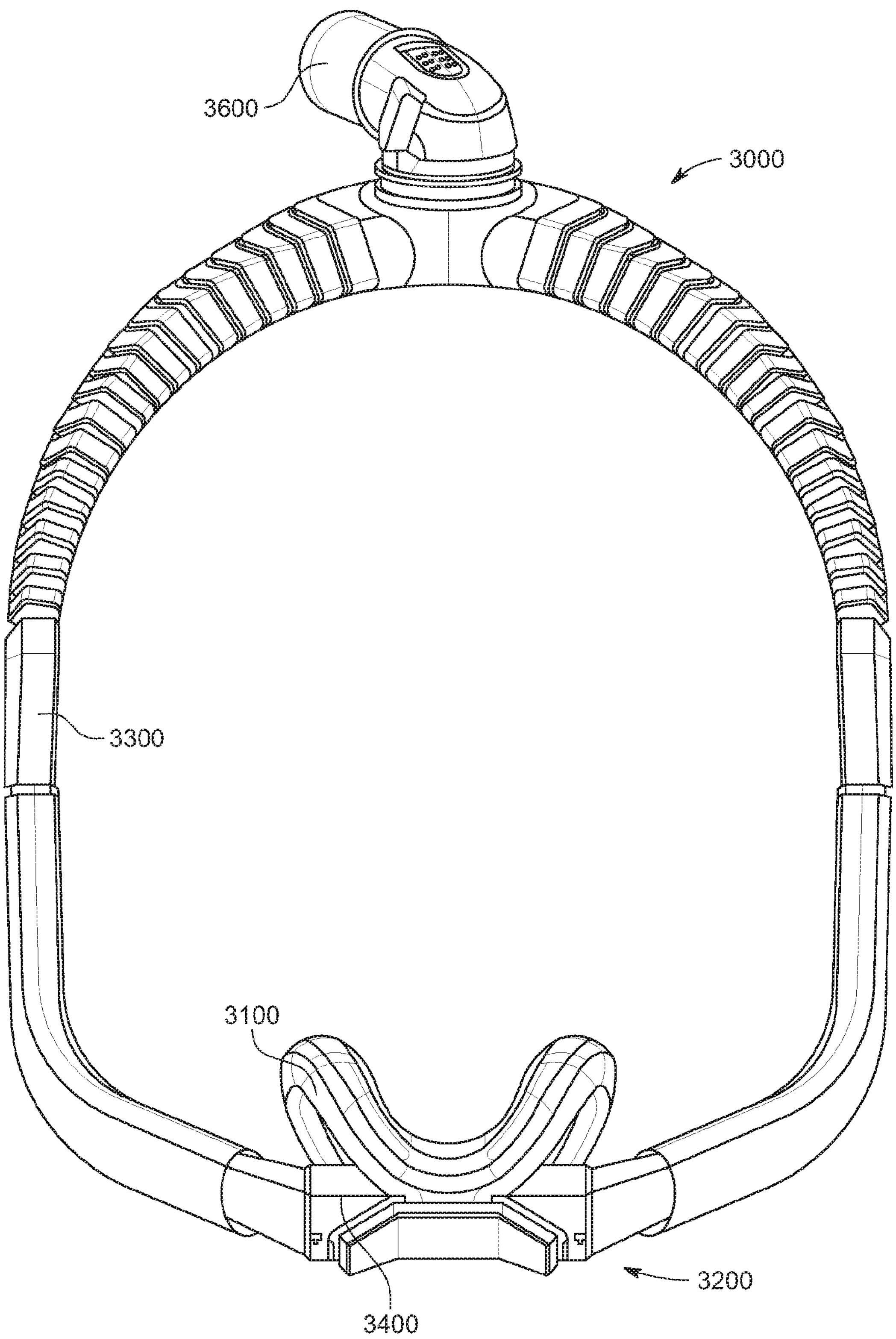

FIG. 7B shows a patient interface 3000, including a vent assembly 3400 in accordance with one form of the present technology.

4.8 Vent Assembly

Figure 8A:
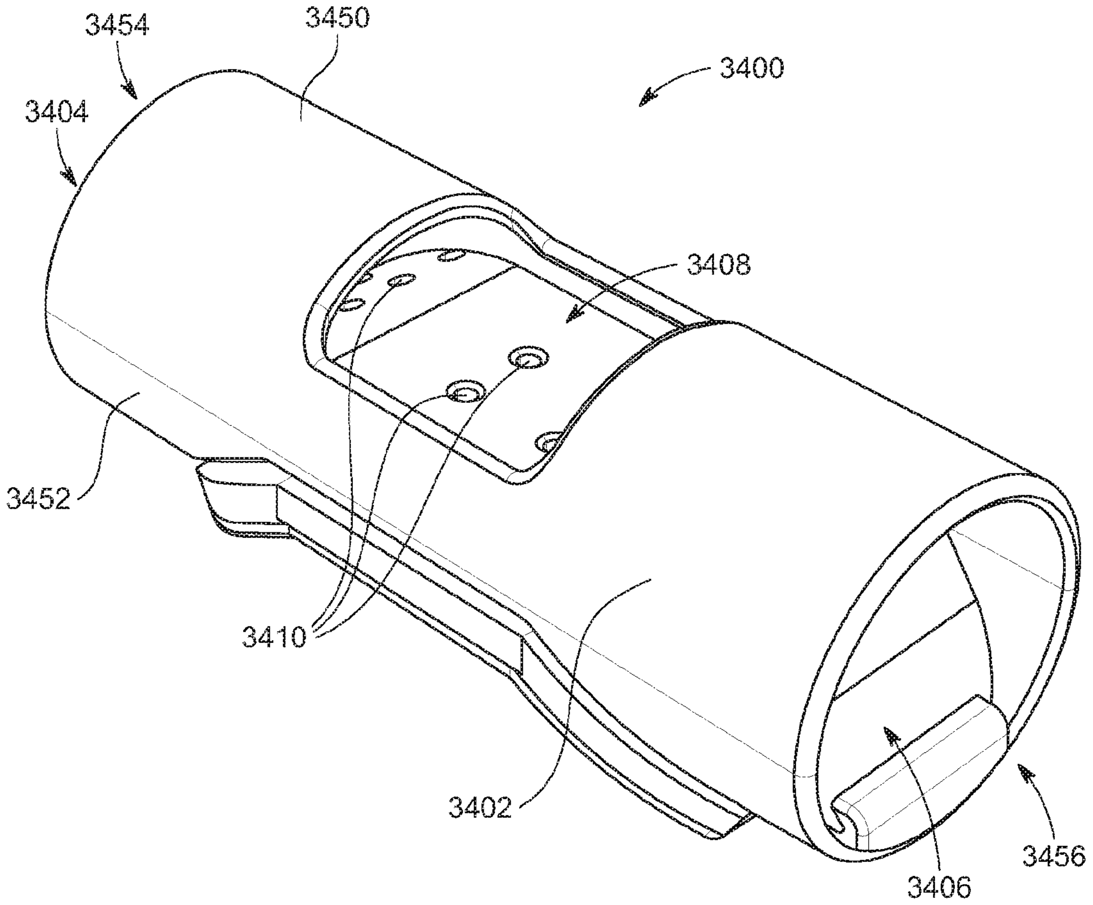

FIG. 8A shows a right superior isometric view of a vent assembly 3400 in accordance with one form of the present technology.

Figure 8B:
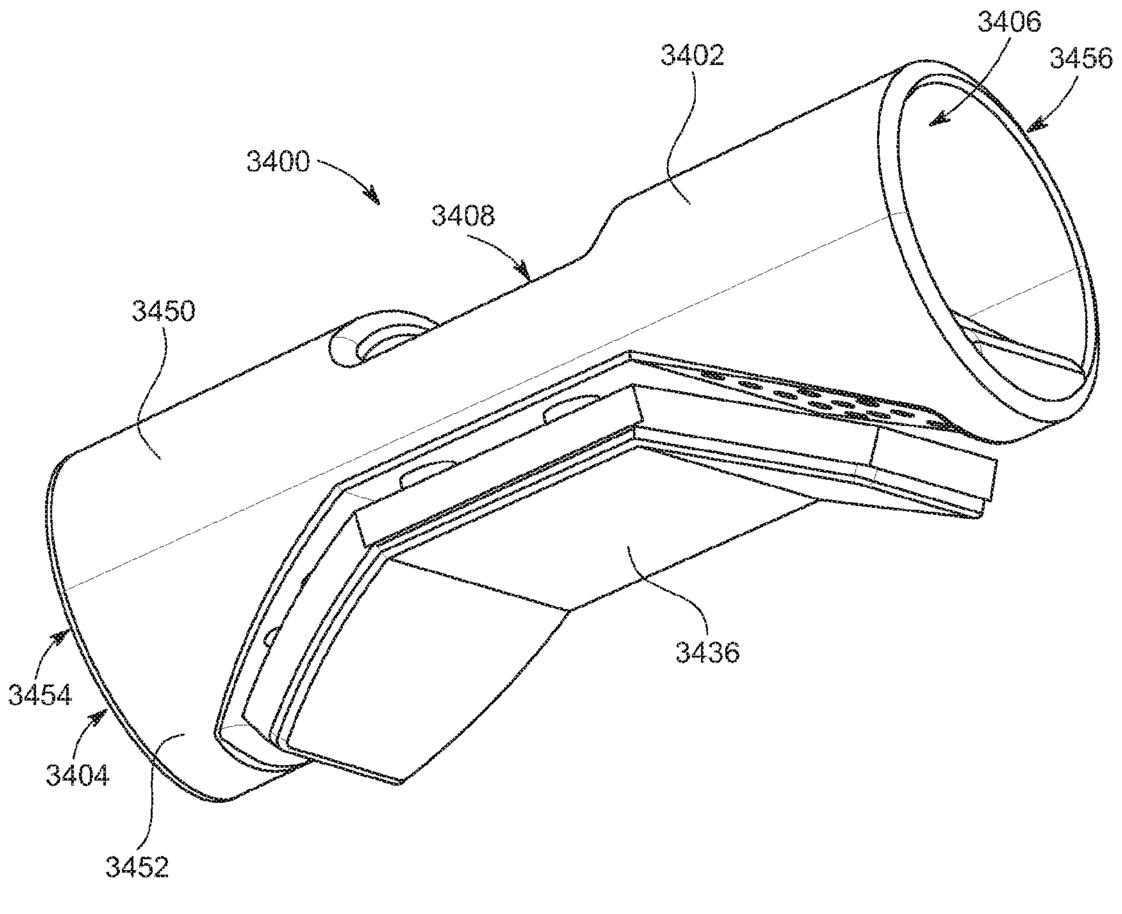

FIG. 8B shows a right inferior isometric view of a vent assembly 3400, including a diffuser 3436, in accordance with one form of the present technology.

Figure 8C:
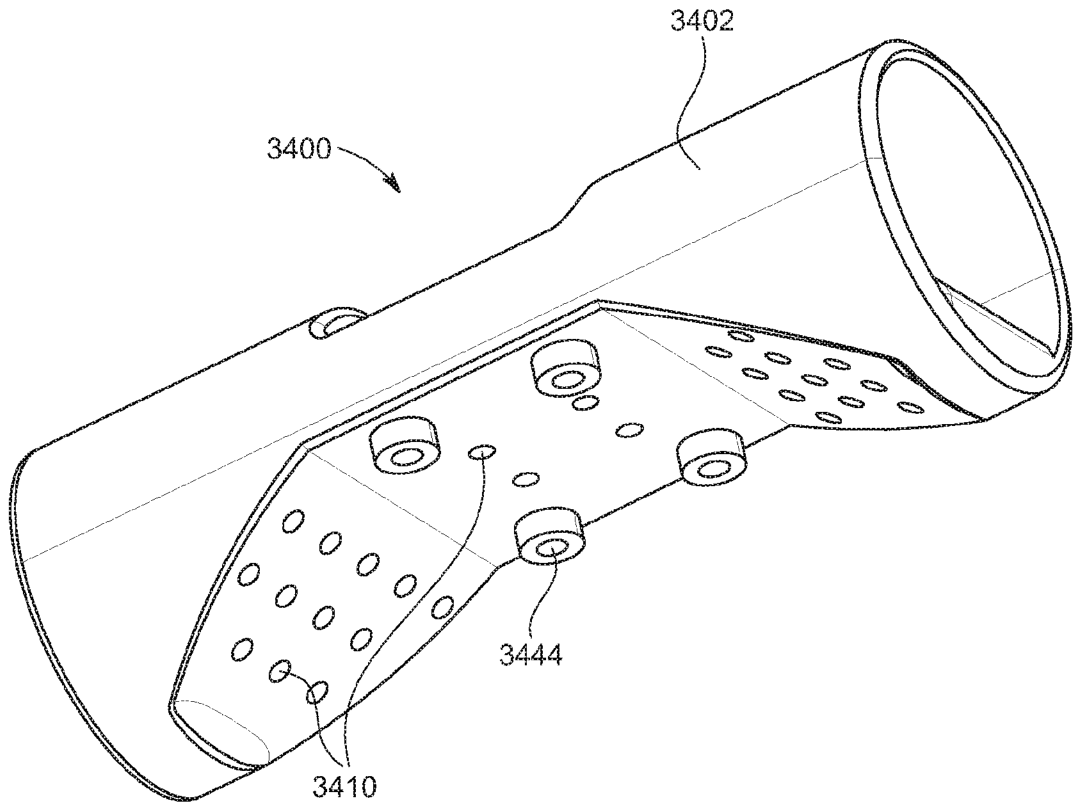

FIG. 8C shows a right inferior isometric view of a vent assembly 3400, in accordance with one form of the present technology, showing the diffuser 3436 removed from the vent body 3402.

Figure 8D:
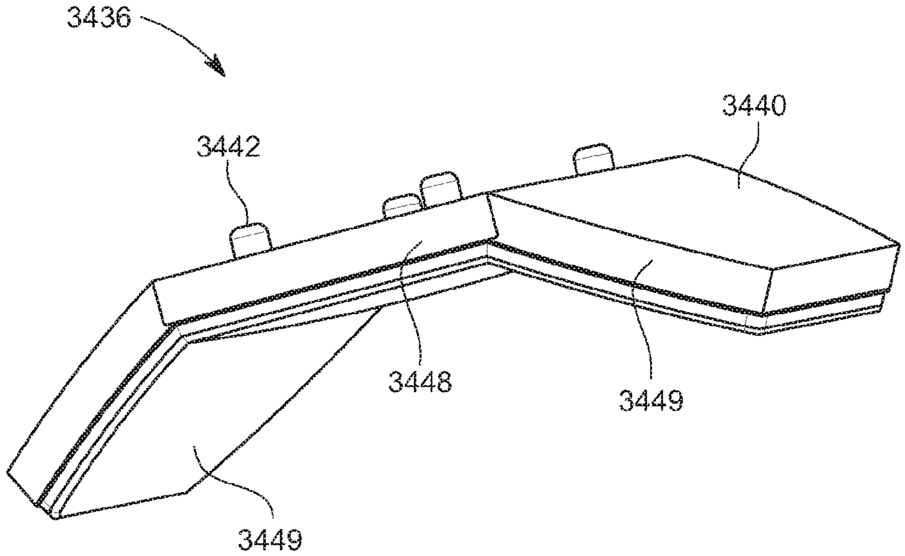

FIG. 8D shows an isometric view of a diffuser 3436, in accordance with one form of the present technology.

Figure 8E:
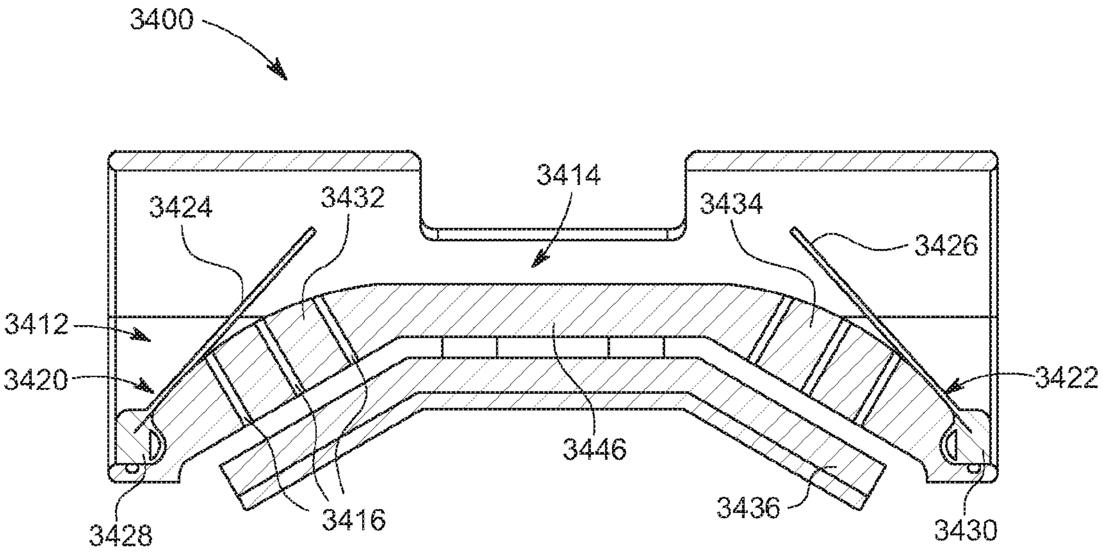

FIG. 8E shows a sectional view of a vent assembly 3400, including a diffuser 3436, in accordance with one form of the present technology, when in a first configuration.

Figure 8F:
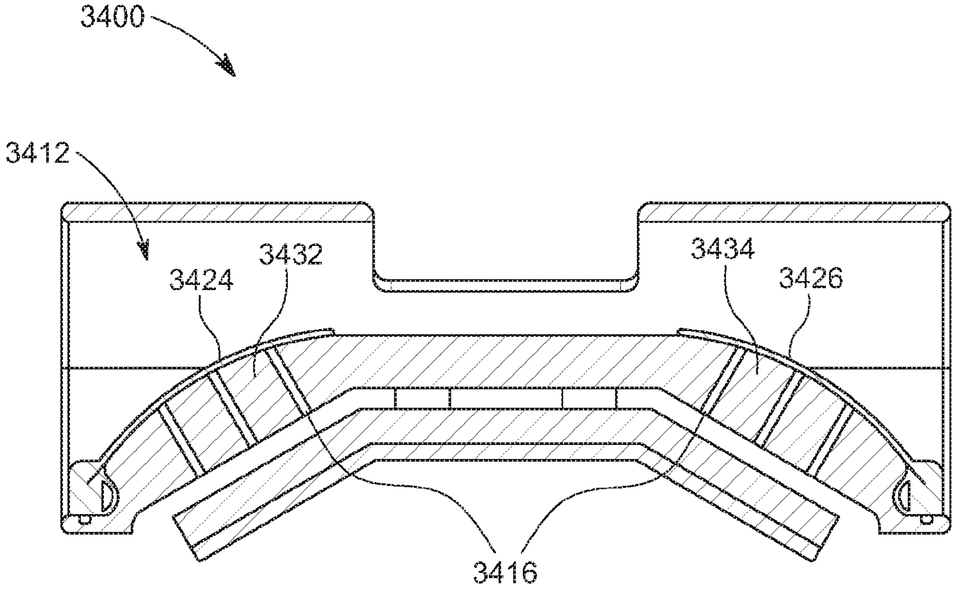

FIG. 8F shows a sectional view of a vent assembly 3400, including a diffuser 3436, in accordance with the form of the present technology shown in FIG. 8E, when in a second configuration.

Figure 8G:
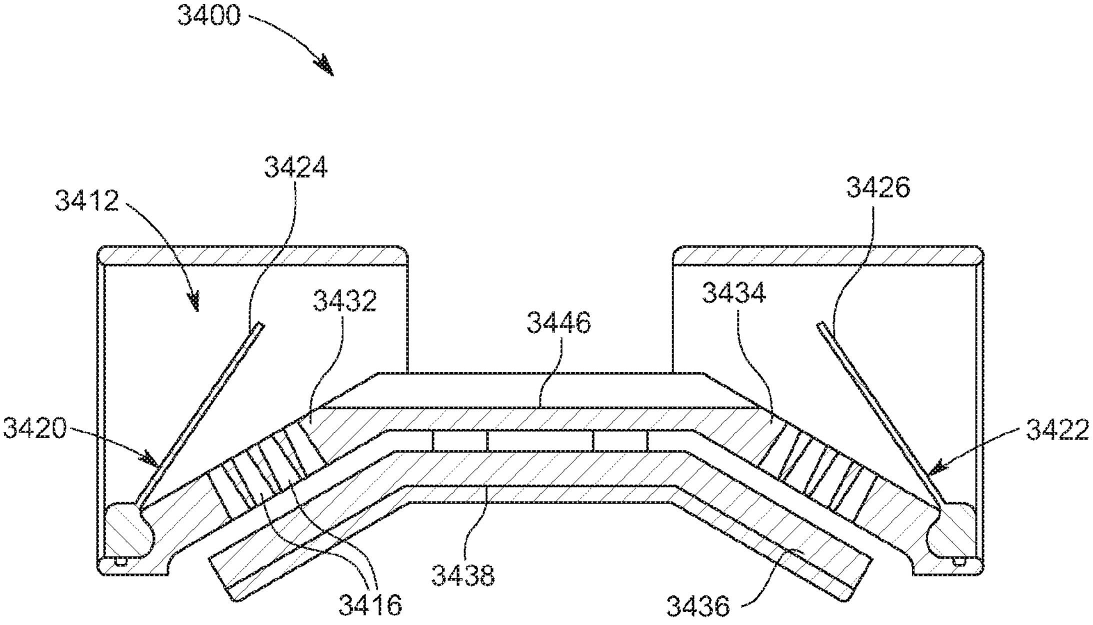

FIG. 8G shows a sectional view of a vent assembly 3400, including a diffuser 3436, in accordance with one form of the present technology, when in a first configuration.

Figure 8H:
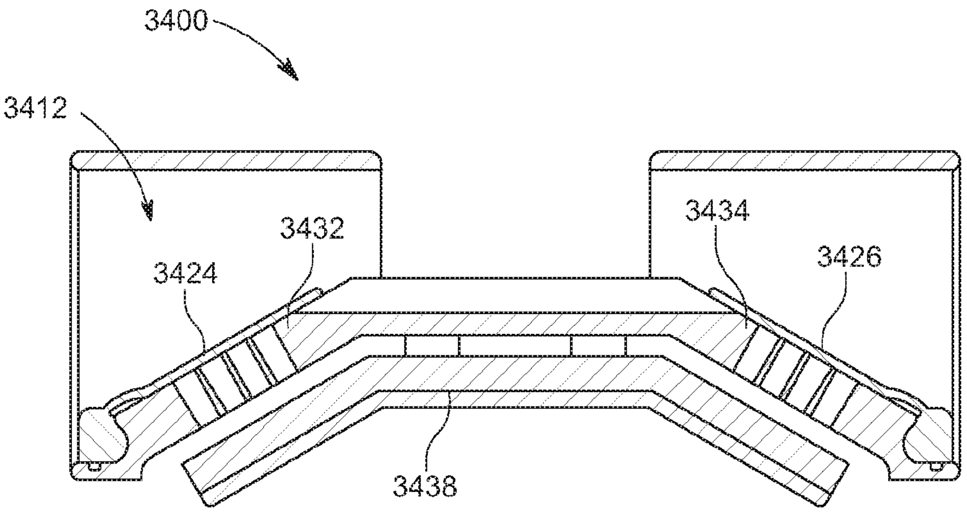

FIG. 8H shows a sectional view of a vent assembly 3400, including a diffuser 3436, in accordance with the form of the present technology shown in FIG. 8G, when in a second configuration.

Figure 8I:
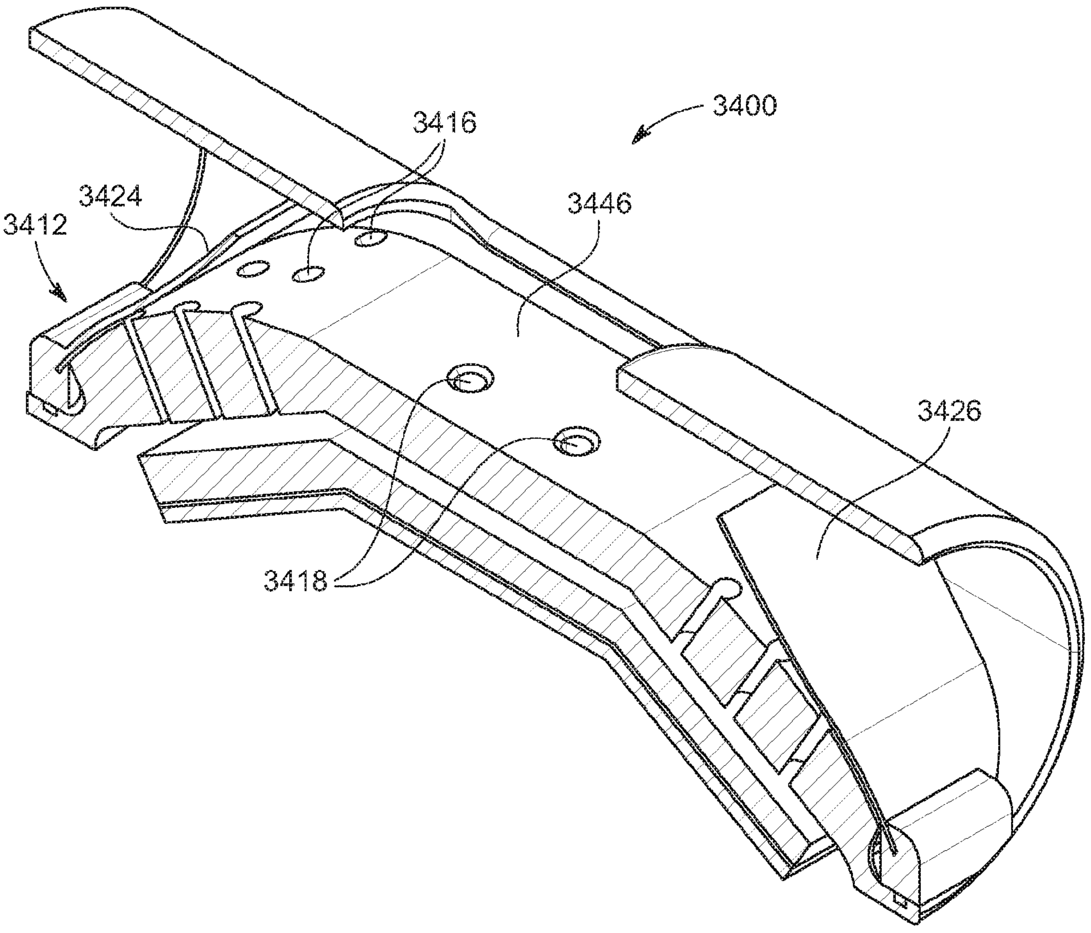

FIG. 8I shows a right superior perspective sectional view of a vent assembly 3400, in accordance with the form of the present technology shown in FIG. 8E.

4.9 Vent Flow Rate

Figure 9A:
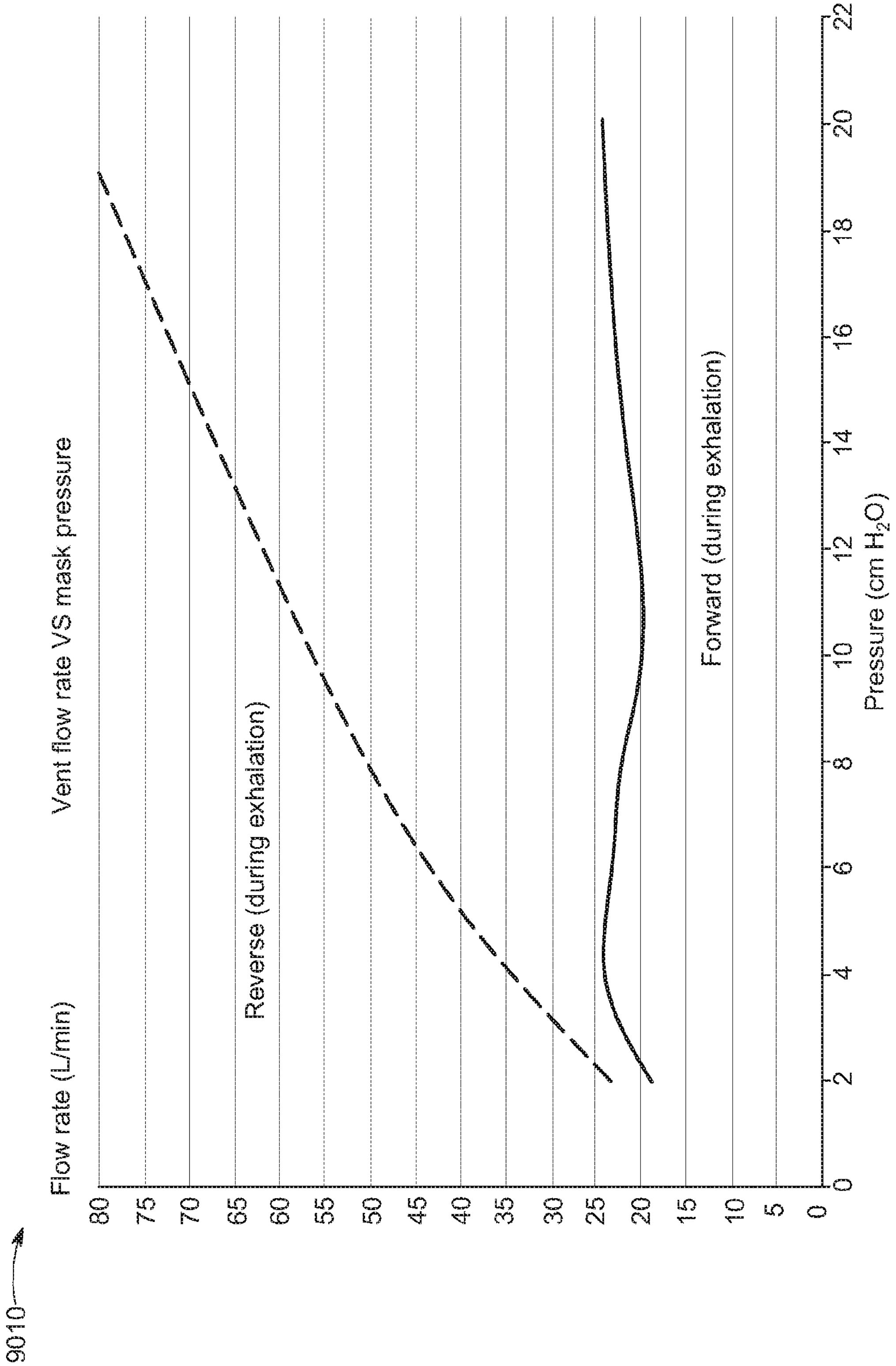

FIG. 9A shows a graph 9010 showing vent flow rate versus supplied air pressure, for both exhalation and inhalation, for a patient interface 3000 in accordance with one form of the present technology.

Figure 9B:
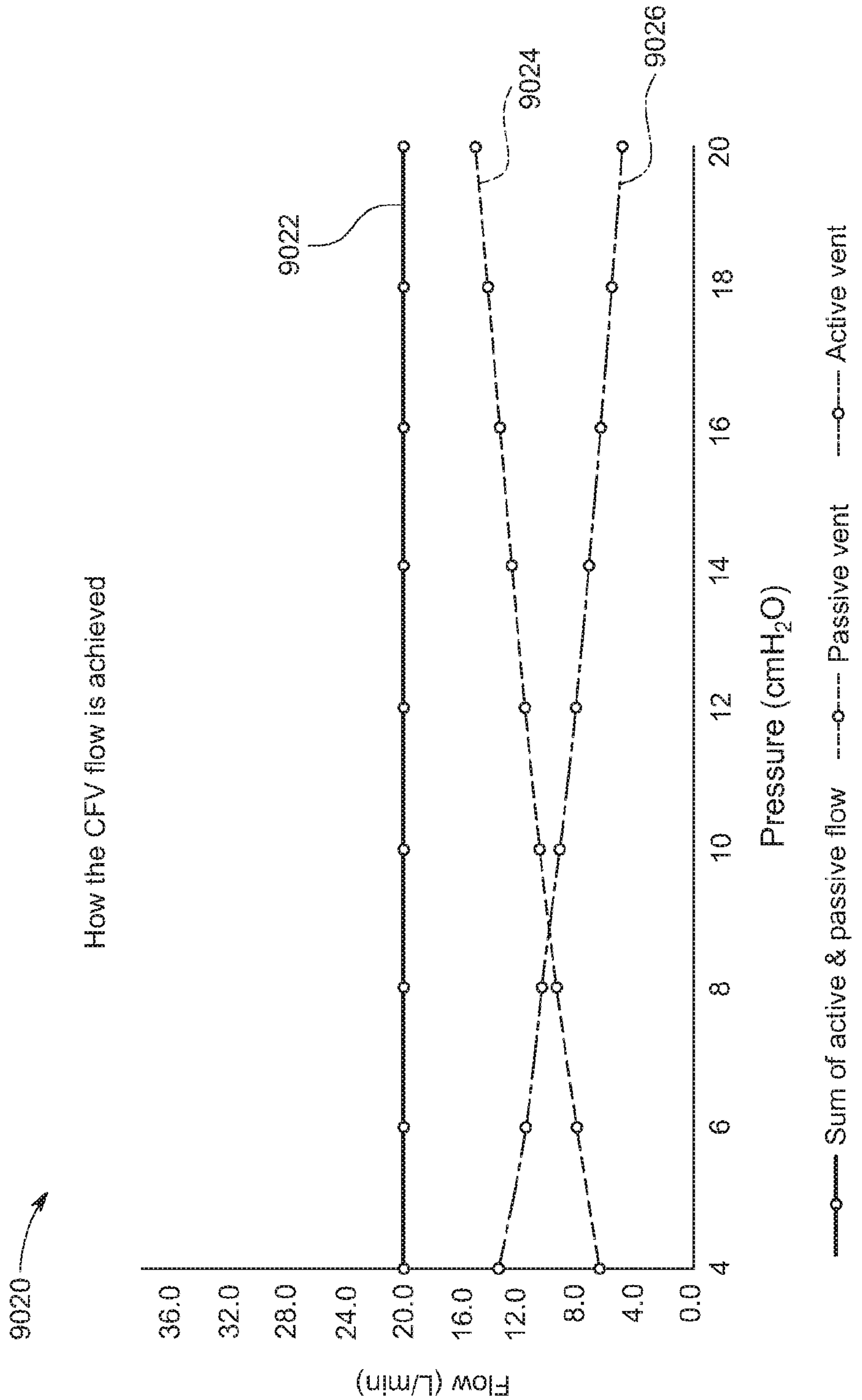

FIG. 9B shows a graph 9020 showing total vent flow rate, as a sum of the vent flow rate for the passive vent holes 3418 and the vent flow rate for the active vent holes 3416, versus supplied air pressure for a patient interface 3000 in accordance with one form of the present technology.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Treatment Systems

In one form, the present technology comprises an apparatus or device for treating a respiratory disorder. The apparatus or device may comprise an RPT device 4000 for supplying pressurised air to the patient 1000 via an air circuit 4170 to a patient interface 3000.

5.3 Patient Interface

A non-invasive patient interface 3000 in accordance with one aspect of the present technology comprises the following functional aspects: a seal-forming structure 3100, a plenum chamber 3200, a positioning and stabilising structure 3300, a vent assembly 3400, one form of connection port 3600 for connection to air circuit 4170, and a forehead support 3700. In some forms a functional aspect may be provided by one or more physical components. In some forms, one physical component may provide one or more functional aspects.

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure of at least 4 $cmH_2O$ with respect to ambient.

The patient interface 3000 in accordance with one form of the present technology is constructed and arranged to be able to provide a supply of air at a positive pressure of at least 10 $cmH_2O$ with respect to ambient.

The patient interface 3000 in accordance with one form of the present technology is constructed and arranged to be able to provide a supply of air at a positive pressure of at least 20 $cmH_2O$ with respect to ambient.

5.3.1 Seal-Forming Structure

In certain forms of the technology, in use, the seal-forming structure 3100 is arranged to surround an entrance to the airways of the patient so as to facilitate the supply of air at positive pressure to the airways.

In one form of the present technology, a seal-forming structure 3100 provides a target seal-forming region, and may additionally provide a cushioning function. The target seal-forming region is a region on the seal-forming structure 3100 where sealing may occur. The region where sealing actually occurs—the actual sealing surface—may change within a given treatment session, from day to day, and from patient to patient, depending on a range of factors including for example, where the patient interface was placed on the face, tension in the positioning and stabilising structure and the shape of a patient's face.

In one form the target seal-forming region is located on an outside surface of the seal-forming structure 3100.

In certain forms of the present technology, the seal-forming structure 3100 is constructed from a biocompatible material, e.g. silicone rubber.

A seal-forming structure 3100 in accordance with the present technology may be constructed from a soft, flexible, resilient material such as silicone.

In certain forms of the present technology, a system is provided comprising more than one a seal-forming structure 3100, each being configured to correspond to a different size and/or shape range. For example, the system may comprise one form of a seal-forming structure 3100 suitable for a large sized head, but not a small sized head and another suitable for a small sized head, but not a large sized head.

5.3.1.1 Sealing Mechanisms

In one form, the seal-forming structure includes a pressure-assisted sealing flange utilizing a pressure-assisted sealing mechanism. In use, the pressure-assisted sealing flange can readily respond to a system positive pressure in the interior of the plenum chamber 3200 acting on its underside to urge it into tight sealing engagement with the face. The pressure-assisted mechanism may act in conjunction with elastic tension in the positioning and stabilising structure.

In one form, the seal-forming structure 3100 comprises a sealing flange and a support flange. The sealing flange comprises a relatively thin member with a thickness of less than about 1 mm, for example about 0.25 mm to about 0.45 mm, which extends around the perimeter of the plenum chamber 3200. Support flange may be relatively thicker than the sealing flange. The support flange is disposed between the sealing flange and the marginal edge of the plenum chamber 3200, and extends at least part of the way around the perimeter. The support flange is or includes a spring-like element and functions to support the sealing flange from buckling in use.

In one form, the seal-forming structure may comprise a compression sealing portion or a gasket sealing portion. In use the compression sealing portion, or the gasket sealing portion is constructed and arranged to be in compression, e.g. as a result of elastic tension in the positioning and stabilising structure.

In one form, the seal-forming structure comprises a tension portion. In use, the tension portion is held in tension, e.g. by adjacent regions of the sealing flange.

In one form, the seal-forming structure comprises a region having a tacky or adhesive surface.

In certain forms of the present technology, a seal-forming structure may comprise one or more of a pressure-assisted sealing flange, a compression sealing portion, a gasket sealing portion, a tension portion, and a portion having a tacky or adhesive surface.

5.3.1.2 Nose Bridge or Nose Ridge Region

In one form, the non-invasive patient interface 3000 comprises a seal-forming structure that forms a seal in use on a nose bridge region or on a nose-ridge region of the patient's face.

In one form, the seal-forming structure includes a saddle-shaped region constructed to form a seal in use on a nose bridge region or on a nose-ridge region of the patient's face.

5.3.1.3 Upper Lip Region

In one form, the non-invasive patient interface 3000 comprises a seal-forming structure that forms a seal in use on an upper lip region (that is, the lip superior) of the patient's face.

In one form, the seal-forming structure includes a saddle-shaped region constructed to form a seal in use on an upper lip region of the patient's face.

5.3.1.4 Chin-Region

In one form the non-invasive patient interface 3000 comprises a seal-forming structure that forms a seal in use on a chin-region of the patient's face.

In one form, the seal-forming structure includes a saddle-shaped region constructed to form a seal in use on a chin-region of the patient's face.

5.3.1.5 Forehead Region

In one form, the seal-forming structure that forms a seal in use on a forehead region of the patient's face. In such a form, the plenum chamber may cover the eyes in use.

5.3.1.6 Nasal Pillows

In one form the seal-forming structure of the non-invasive patient interface 3000 comprises a pair of nasal puffs, or nasal pillows, each nasal puff or nasal pillow being constructed and arranged to form a seal with a respective naris of the nose of a patient.

Nasal pillows in accordance with an aspect of the present technology include: a frusto-cone, at least a portion of which forms a seal on an underside of the patient's nose, a stalk, a flexible region on the underside of the frusto-cone and connecting the frusto-cone to the stalk. In addition, the structure to which the nasal pillow of the present technology is connected includes a flexible region adjacent the base of the stalk. The flexible regions can act in concert to facilitate a universal joint structure that is accommodating of relative movement both displacement and angular of the frusto-cone and the structure to which the nasal pillow is connected. For example, the frusto-cone may be axially displaced towards the structure to which the stalk is connected.

5.3.1.7 Nasal Cradle

In the forms of the technology shown in FIG. 7A and FIG. 7B the seal-forming structure 3100 of the non-invasive patient interface 3000 is in the form of a nasal cradle cushion. In such a form the seal-forming structure 3100 may seal around an inferior periphery of the nose. In other words, seal may be formed with the lower surfaces of the patient's nose, e.g. surfaces of the patient's nose facing in a generally inferior direction. The seal-forming structure 3100 may form a seal particularly around the ala and tip of the nose. In the form of technology shown in these figures, a superior-most region of sealing of an anterior portion of the seal-forming structure 3100 is a region of the nose inferior to the pronasale. That is, the seal-forming structure 3100 may be configured so as not to seal to the tip of the patient's nose or any region superior to the tip. A nasal cradle cushion may seal around both nares with a single orifice or the seal-forming structure 3100 may form two orifices, each configured to supply breathable gas in use to one of the patient's nares.

5.3.2 Plenum Chamber

In certain forms of the technology, the plenum chamber 3200 is a portion of patient interface 3000 having walls at least partially enclosing a volume of space, the volume having air therein pressurised above atmospheric pressure in use.

The plenum chamber 3200 may in some forms have a perimeter that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3100. The seal-forming structure 3100 may extend in use about the entire perimeter of the plenum chamber 3200. In some forms, the plenum chamber 3200 and the seal-forming structure 3200 are formed from a single homogeneous piece of material.

In certain forms of the present technology, the plenum chamber 3200 does not cover the eyes of the patient in use. In other words, the eyes are outside the pressurised volume defined by the plenum chamber. Such forms tend to be less obtrusive and/or more comfortable for the wearer, which can improve compliance with therapy.

In certain forms of the present technology, the plenum chamber 3200 is constructed from a transparent material, e.g. a transparent polycarbonate. The use of a transparent material can reduce the obtrusiveness of the patient interface, and help improve compliance with therapy. The use of a transparent material can aid a clinician to observe how the patient interface is located and functioning.

In certain forms of the present technology, the plenum chamber 3200 is constructed from a translucent material. The use of a translucent material can reduce the obtrusiveness of the patient interface, and help improve compliance with therapy.

In some forms, the patient interface 3000 comprises a cushion module 3150, which may be configured to contact the face of the patient in use and is cushioned, e.g. being made of a soft material, for comfort. The cushion module 3150 may comprise the seal-forming structure 3100 and at least part of the plenum chamber 3200. In some forms, the cushion module 3150 may be an integrally formed component, for example a molded component of silicone that is attachable to and removable from the rest of the patient interface 3000 in a modular fashion. For example, in the case of the form of the technology shown in FIGS. 7A and 7B, the seal-forming structure 3100 and the plenum chamber 3200 together form the cushion module 3150.

5.3.3 Positioning and Stabilising Structure

The seal-forming structure 3100 of the patient interface 3000 of the present technology may be held in a sealing position in use by the positioning and stabilising structure 3300.

In one form the positioning and stabilising structure 3300 provides a retention force at least sufficient to overcome the effect of the positive pressure in the plenum chamber 3200 to lift off the face.

In one form the positioning and stabilising structure 3300 provides a retention force to overcome the effect of the gravitational force on the patient interface 3000.

In one form the positioning and stabilising structure 3300 provides a retention force as a safety margin to overcome the potential effect of disrupting forces on the patient interface 3000, such as from tube drag, or accidental interference with the patient interface.

In one form of the present technology, a positioning and stabilising structure 3300 is provided that is configured in a manner consistent with being worn by a patient while sleeping. In one example the positioning and stabilising structure 3300 has a low profile, or cross-sectional thickness, to reduce the perceived or actual bulk of the apparatus. In one example, the positioning and stabilising structure 3300 comprises at least one strap having a rectangular cross-section. In one example the positioning and stabilising structure 3300 comprises at least one flat strap.

In one form of the present technology, a positioning and stabilising structure 3300 is provided that is configured so as not to be too large and bulky to prevent the patient from lying in a supine sleeping position with a back region of the patient's head on a pillow.

In one form of the present technology, a positioning and stabilising structure 3300 is provided that is configured so as not to be too large and bulky to prevent the patient from lying in a side sleeping position with a side region of the patient's head on a pillow.

In one form of the present technology, a positioning and stabilising structure 3300 is provided with a decoupling portion located between an anterior portion of the positioning and stabilising structure 3300, and a posterior portion of the positioning and stabilising structure 3300. The decoupling portion does not resist compression and may be, e.g. a flexible or floppy strap. The decoupling portion is constructed and arranged so that when the patient lies with their head on a pillow, the presence of the decoupling portion prevents a force on the posterior portion from being transmitted along the positioning and stabilising structure 3300 and disrupting the seal.

In one form of the present technology, a positioning and stabilising structure 3300 comprises a strap constructed from a laminate of a fabric patient-contacting layer, a foam inner layer and a fabric outer layer. In one form, the foam is porous to allow moisture, (e.g., sweat), to pass through the strap. In one form, the fabric outer layer comprises loop material to engage with a hook material portion.

In certain forms of the present technology, a positioning and stabilising structure 3300 comprises a strap that is extensible, e.g. resiliently extensible. For example the strap may be configured in use to be in tension, and to direct a force to draw a seal-forming structure into sealing contact with a portion of a patient's face. In an example the strap may be configured as a tie.

In one form of the present technology, the positioning and stabilising structure comprises a first tie, the first tie being constructed and arranged so that in use at least a portion of an inferior edge thereof passes superior to an otobasion superior of the patient's head and overlays a portion of the parietal bone without overlaying the occipital bone.

In one form of the present technology suitable for a nasal-only mask or for a full-face mask, the positioning and stabilising structure includes a second tie, the second tie being constructed and arranged so that in use at least a portion of a superior edge thereof passes inferior to an otobasion inferior of the patient's head and overlays or lies inferior to the occipital bone of the patient's head.

In one form of the present technology suitable for a nasal-only mask or for a full-face mask, the positioning and stabilising structure includes a third tie that is constructed and arranged to interconnect the first tie and the second tie to reduce a tendency of the first tie and the second tie to move apart from one another.

In certain forms of the present technology, a positioning and stabilising structure 3300 comprises a strap that is bendable and e.g. non-rigid. An advantage of this aspect is that the strap is more comfortable for a patient to lie upon while the patient is sleeping.

In certain forms of the present technology, a positioning and stabilising structure 3300 comprises a strap constructed to be breathable to allow moisture vapour to be transmitted through the strap, In certain forms of the present technology, a system is provided comprising more than one positioning and stabilizing structure 3300, each being configured to provide a retaining force to correspond to a different size and/or shape range. For example the system may comprise one form of positioning and stabilizing structure 3300 suitable for a large sized head, but not a small sized head, and another. suitable for a small sized head, but not a large sized head.

5.3.3.1 Headgear Tubing

In some forms of the present technology the positioning and stabilising structure 3300 comprises one or more tubes 3350 that deliver pressurised air received from a conduit forming part of the air circuit 4170 from the RPT device to the patient's airways, for example through the plenum chamber 3200 and seal-forming structure 3100. In the forms of the present technology illustrated in FIG. 7A and FIG. 7B, the positioning and stabilising structure 3300 comprises two tubes 3350 that deliver air to the seal-forming structure 3100 from the air circuit 4170. The tubes 3350 are an integral part of the positioning and stabilising structure 3300 of patient interface 3000, i.e. the tubes 3350 function to position and stabilise the seal-forming structure 3100 of the patient interface to the appropriate part of the patient's face (for example, the nose and/or mouth). This allows the conduit of air circuit 4170 providing the flow of pressurised air to connect to a connection port 3600 of the patient interface in a position other than in front of the patient's face, which may be unsightly or uncomfortable to some people. While a pair of tubes 3350 have some advantages (described below), in some examples, the positioning and stabilising structure 3300 comprises only a single tube 3350 configured to overlie the patient's head on one side. In such examples, a strap or other stabilising component may be provided to the other side of the patient's head between the top end of the single tube 3350 and the seal-forming structure 3100, to provide balanced forces on the seal-forming structure 3100.

Since air can be contained and passed through headgear tubing 3350 in order to deliver pressurised air from the air circuit 4170 to the patient's airways, the positioning and stabilising structure 3300 may be described as being inflatable. It will be understood that an inflatable positioning and stabilising structure 3300 does not require all components of the positioning and stabilising structure 3300 to be inflatable. For example, in the example shown in FIG. 7A, the positioning and stabilising structure 3300 comprises the headgear tubing 3350, which is inflatable, and the strap 3310, which is not inflatable.

In certain forms of the present technology, the patient interface 3000 may comprise a connection port 3600 located proximal a top, side or rear portion of a patient's head when the patient interface 3000 is worn. For example, in the form of the present technology illustrated in FIG. 7A, the connection port 3600 is located on top of the patient's head when the patient interface 3000 is worn. In this example the patient interface 3000 comprises an elbow 3610 to which the connection port 3600 is provided. The elbow 3610 may swivel with respect to the positioning and stabilising structure 3300 and functions to decouple movement of a conduit connected to the connection port 3600 from the positioning and stabilising structure 3300. Additionally, or alternatively, a conduit connected to the connection port 3600 may swivel with respect to the elbow 3610. In the illustrated example, elbow 3610 comprises a swivelling conduit connector to which a conduit of the air circuit 4170 is able to connect such that the conduit can rotate about its longitudinal axis with respect to the elbow 3610. The connection port 3600 may comprise a fluid connection opening. In some examples the air circuit 4170 may connect to the fluid connection opening. The elbow 3610 may rotatably connect to the fluid connection opening or to a ring received in the fluid connection opening.

Patient interfaces in which the connection port is not positioned in front of the patient's face may be advantageous as some patients find a conduit that connects to a patient interface in front of the face to be unsightly and obtrusive. For example, a conduit connecting to a patient interface in front of the face may be prone to being tangled up in bedclothes or bed linen, particularly if the conduit extends downwardly from the patient interface in use. Forms of the technology with a patient interface with a connection port positioned proximate the top of the patient's head in use may make it easier or more comfortable for a patient to lie or sleep in one or more of the following positions: in a side or lateral position; in a supine position (i.e. on their back, facing generally upwards); and in a prone position (i.e. on their front, facing generally downwards). Moreover, connecting a conduit to the front of a patient interface may exacerbate a problem known as tube drag, wherein the conduit may provide an undesired drag force upon the patient interface thereby causing dislodgement away from the face.

In the forms of the present technology illustrated in FIG. 7A and FIG. 7B, the positioning and stabilising structure 3300 comprises two tubes 3350, each tube 3350 being positioned in use on a different side of the patient's head and extending across the respective cheek region, above the respective ear (superior to the otobasion superior on the patient's head) to the elbow 3610 on top of the head of the patient 1000. This form of technology may be advantageous because, if a patient sleeps with their head on its side and one of the tubes is compressed to block or partially block the flow of gas along the tube, the other tube remains open to supply pressurised gas to the patient. In other examples of the technology, the patient interface 3000 may comprise a different number of tubes, for example one tube, or three or more tubes. In one example in which the patient interface has one tube 3350, the single tube 3350 is positioned on one side of the patient's head in use (e.g. across one cheek region) and a strap forms part of the positioning and stabilising structure 3300 and is positioned on the other side of the patient's head in use (e.g. across the other region) to assist in securing the patient interface 3000 on the patient's head.

In the forms of the technology shown in FIG. 7A and FIG. 7B, the two tubes 3350 are fluidly connected at their upper ends to each other and to connection port 3600. In one embodiment, the two tubes are integrally formed while in other embodiments the tubes are separate components that are connected together in use and may be disconnected, for example for cleaning or storage. Where separate tubes are used they may be indirectly connected together, for example each may be connected to a T-shaped conduit having two conduit arms each fluidly connectable to the tubes 3350 and a third conduit arm or opening acting as the connection port 3600 and connectable in use to the air circuit 4170. The connection port 3600 may comprise an elbow 3610 received in fluid connection opening 3390 at the centre of two integrally formed tubes 3350. The elbow 3610 may be received in a ring in the fluid connection opening 3390 and may be configured to swivel within the ring. The fluid connection opening 3390 may be also considered a connection port 3600 itself.

The tubes 3350 may be formed of a semi-rigid material such as an elastomeric material, e.g. silicone. For example, the tubes 3350, from the left-side non-extendable tube section 3363 to the right side non-extendable tube section 3363, may be formed (e.g., by molding) from a single homogeneous piece of material, such as silicone. The tubes may have a natural, preformed shape and be able to be bent or moved into another shape if a force is applied to the tubes. For example, the tubes may be generally arcuate or curved in a shape approximating the contours of a patient's head between the top of the head and the nasal or oral region.

The positioning and stabilising structure 3300 in some examples may comprise sleeves 3364 around the tubes 3350. For example, as shown in FIG. 7A, sleeves 3364 are provided to the non-extendable tube sections 3363. In some examples, the patient interface 3000 may not comprise sleeves 3364 and in other examples the patient interface 3000 may comprise sleeves 3364 that cover more, or all, of the tubes 3350. The sleeves 3364 may be formed to fit to the curved shape of the tubes 3350. In some examples, the sleeves 3364 are formed from a smooth fabric. The sleeves 3364 may be more comfortable against the patient's face than the tube 3350 without any covering.

As described in U.S. Pat. No. 6,044,844, the contents of which are incorporated herein, the tubes 3350 may be crush-resistant to avoid obstructing the flow of breathable gas through the tubes if either is crushed during use, for example if it is squashed between a patient's face and pillow. Crush-resistant tubes may not be necessary in all cases as the pressurised gas in the tubes may act as a splint to prevent or at least restrict crushing of the tubes 3350 during use. A crush-resistant tube may be advantageous where only a single tube 3350 is present as if the single tube becomes blocked during use the flow of gas would be restricted and therapy will stop or reduce in efficacy.

In certain forms of the technology, one or more portions of the tubes 3350 may be rigidised by one or more rigidising or stiffening elements. Examples of rigidising elements include: sections of the tubes 3350 that are comparatively thicker than other sections; sections of the tubes 3350 that are formed from a material that is comparatively more rigid that the material forming other sections; and a rigid member attached to the inside, outside or embedded in a section of tube. The use of such rigidising elements helps to control how the positioning and stabilising structure 3300 will function in use, for example where the tubes 3350 is more likely to deform if forces are applied to them and where the shape of the tubes 3350 is more likely to be maintained if forces are applied. The selection of where such rigidising elements are positioned in the tubes 3350 can therefore help to promote comfort when the patient interface 3000 is worn and can help to maintain a good seal at the seal-forming structure 3100 during use. Rigidising or stiffening elements may be in positioning and stabilising structures 3300 which are configured to support relatively heavy seal-forming structures such as full face or oro-nasal cushion assemblies.

The tubes 3350 in the forms of the technology shown in FIG. 7A and FIG. 7B have a length of between 15 and 30 cm each, for example between 20 and 27 cm each. In one example each of the tubes are around 26 cm long. In another example each of the tubes is around 23 cm long. The length of the tubes is selected to be appropriate for the dimensions of the heads of typical patients, for example the distance between the region proximate the top of the head where the upper end of the tubes 3350 are situated, and the region proximate the openings to the patient's airways at which the lower end of the tubes 3350 connect to the cradle cushion module 3150 (or alternatively pillows cushion module) when following a generally arcuate path down the sides of the heads and across the patient's cheek region such as is shown in FIG. 7A. The patient interface 3000 may be configured so that the length of the tubes 3350 can be varied in some forms of the technology and the above lengths may apply to the tube in a contracted, stretched or neutral state. It will be appreciated that the length of the tubes 3350 will depend on the length of other components in the patient interface 3000, for example the length of arms of a T-shaped conduit to which the upper ends of tubes 3350 connect and/or the size of the plenum chamber 3200.

5.3.4 Vent Assembly

In certain forms, for example as shown in FIGS. 7A, 7B and 8A to 8I, the patient interface 3000 includes a vent assembly 3400 constructed and arranged to allow for the washout of exhaled gases, e.g. carbon dioxide.

In certain forms, the vent assembly 3400 is configured to deliver a flow of breathable gas at a positive pressure to an airway entrance of a patient, for example by receiving the flow of breathable gas from one component of the patient interface 3000 and delivering the flow of breathable gas to another component of the patient interface 3000. The vent assembly may also be further configured to allow a flow of exhaled gas from the airway of a patient, which may be called a vent flow, to exit the vent assembly 3400 to ambient.

In certain forms, the vent assembly 3400 is configured to allow a continuous vent flow from an interior of the plenum chamber 3200 to ambient whilst the pressure within the plenum chamber is positive with respect to ambient. The vent assembly 3400 is configured such that the vent flow rate has a magnitude sufficient to reduce rebreathing of exhaled $CO_2$ by the patient while maintaining the therapeutic pressure in the plenum chamber in use.

As is the case with the forms of the technology shown in FIGS. 7A, 7B and 8A to 8I, the vent assembly 3400 may form part of the plenum chamber 3200. For example, the vent assembly 3400 may enclose a volume of space containing pressurised air during use of the patient interface 3000. In some forms, for example as shown in FIGS. 7A and 7B, the vent assembly 3400 and another component, for example a cushion module 3150, together form the plenum chamber 3200. The cushion module 3150 may also comprise the seal-forming structure 3100.

In one form of the present technology, the patient interface 3000 is configured so that, in use, the vent assembly 3400 is located proximate the airway entrance of a patient, for example proximate the nasal entrance as in the case of the patient interface 3000 of FIGS. 7A and 7B. In these forms, the vent assembly 3400 is positioned directly in front of the patient's nares. The seal-forming structure 3100, constructed and arranged to form a seal with a region of the patient's face surrounding the airway entrance, includes an aperture therein. The aperture is fluidly connected to the vent assembly 3400, such that the flow of breathable gas delivered to the airway entrance of the patient from the vent assembly 3400 and a flow of exhaled gas delivered away from the airway of the patient to the vent assembly 3400 passes through the aperture of the seal-forming structure 3100.

It has been explained above that, in certain forms of the technology, the positioning and stabilising structure 3300 comprises one or more tubes 3350 that deliver pressurised air received from a conduit forming part of the air circuit 4170 from the RPT device to the patient's airways. A vent assembly 3400 configured for use in a patient interface 3000 comprising a positioning and stabilising structure 3300 of this type is shown in FIG. 7B. The vent assembly 3400 shown in these figures is described in the following passages.

The vent assembly 3400 in the form of the technology shown in FIG. 7B is further configured to fluidly connect with the gas delivery tubes 3350 of the air circuit 4170 in order to receive the flow of breathable gas from the gas delivery tubes 3350 in use. The gas delivery tubes may comprise a pair of tubes 3350, in the form of conduit headgear.

In one form of the present technology, the vent assembly 3400 consists of a vent body 3402 which defines a vent chamber 3414. The vent body 3402 may be configured to form a first inlet 3404, a second inlet 3406, an opening 3408, a plurality of vent holes 3410, and to include a valve 3412, which is a dual valve arrangement in the form of the technology illustrated in FIGS. 8A to 8C and FIGS. 8E to 8I. The vent body may be further configured to receive a diffuser body. These aspects of the vent assembly 3400 will now be described in greater detail.

5.3.4.1 Vent Body

In one form of the present technology, the vent assembly 3400 includes a vent body 3402. In the forms illustrated in FIGS. 8A to 8C and FIGS. 8E to 8I the vent body 3402 is generally tube-shaped and is defined at least in part by, but not restricted to, a patient-facing surface 3450, a non-patient-facing surface 3452, a first side 3454 and a second side 3456. In FIGS. 8A and 8B these surfaces and sides are labelled, with the patient-facing surface 3450 generally facing upwards in the figures, the non-patient-facing surface 3452 generally facing downwards, and the first side 3454 and the second side 3456 being the lateral ends of the vent body 3402.

The vent body 3402 defines a vent chamber 3414, comprising a volume of space within the boundary of the vent body 3402. In the illustrated form, the vent body is configured to have an outer profile that is generally cylindrical in shape. In use, as can be seen from FIG. 7B, the longitudinal axis of the cylindrical vent body 3402 is oriented perpendicular to the sagittal plane. However, it should be appreciated that the vent body 3402 could generally take the form of other tubular shapes such as tubes having generally oval, rectangular or square cross-sections. In other forms the vent body 3402 may be another shape, e.g. non-tubular. In the illustrated form, the non-patient-facing surface 3452 of the vent body 3402 has a cavity to enable a diffuser 3436 to be provided to the vent assembly 3400. The cavity means that the vent body 3402 in this form is not entirely cylindrical.

The vent body 3402 may form part of the plenum chamber 3200. For example, the vent chamber 3414 inside the vent body 3402 may, together with the volume inside a cushion module 3150 provided to the vent body 3402, form the volume contained inside the plenum chamber 3200. The vent body 3401 is configured to contain pressurised air during use of the patient interface 3000.

The vent body 3402 may be configured to define gas inlets, for example two gas inlets. The inlets are described in more detail below.

The patient-facing surface 3450 of the vent body 3402 may be configured to define an opening 3408 to fluidly connect in use to the seal-forming structure 3100. The opening 3408 is described in more detail below.

The non-patient-facing surface 3452 of the vent body 3402 may be configured to include a plurality of vent holes 3410, which may include active vent holes 3416 and may include passive vent holes 3418. The non-patient-facing surface of the vent body 3402 may also include one or more vent body connectors 3444 configured to enable a diffuser 3436 to be provided to the vent assembly 3400.

In certain forms of the technology the vent body 3402 may be constructed from a plastics material such as polycarbonate. Other materials may be used in other forms of the technology.

5.3.4.2 Inlets

In one form of the present technology, the vent body 3402 is configured to define two gas inlets. A first inlet 3404, which may be located on a first side 3454 of the vent body 3402, is configured to receive a first inlet flow of breathable gas into the vent chamber 3414. A second inlet 3406, which may be located on the second side 3456 of the vent body 3402, the second side 3456 being opposite the first side 3454, is configured to receive a second inlet flow of breathable gas into the vent chamber 3414. The sides of the vent body 3402 on which the first inlet 34040 and second inlet 3406 are located may be understood to be the lateral sides of the vent body 3402 when the patient interface 3000 is in use, i.e. the sides of the vent body 3402 distal from the mid-sagittal plane in use.

In the forms of the technology illustrated in FIGS. 8A to 8C and FIGS. 8E to 8I, the vent body 3402 is configured so that the first inlet 3404 fluidly connects in use to a first gas delivery tube of a pair of gas delivery tubes 3350 and so that the second inlet 3406 fluidly connects in use to a second gas delivery tube of a pair of gas delivery tubes 3350. The pair of gas delivery tubes 3350 of the patient interface 3000 form part of the air circuit 4170, which provides the flow of pressurised air into the vent chamber 3414 through the first and second inlets.

In the forms of the technology illustrated in FIGS. 8A to 8C and FIGS. 8E to 8I, the first inlet 3404 and second inlet 3406 are substantially circular. However, in other forms of the present technology, the first and second inlets may be configured with another shape, for example a shape that is substantially oval, rectangular or square. It will be understood that the shape of the first inlet 3404 and second inlet 3406 may depend on the tubular shape of the vent body 3402 and/or on the shape of the ends of the gas delivery tubes 3350 that connect to the inlets in use. For example, the shape of the inlets may be complementary to the shape of the ends of the gas delivery tubes 3350.

In certain forms of the technology the first and second inlets 3404 and 3406 may be configured to connect to the first and second gas delivery tubes 3350 by means of a threaded, friction-fit or snap-fit connection. The vent body 3402 and/or the gas delivery tubes 3350 may be shaped and/or configured (for example may comprise additional components) to facilitate the means of connection. For example, they may comprise any one or more of the following: lugs; screw threads; depressions; O-rings; and seals.

5.3.4.3 Opening

In one form of the present technology, the vent body 3402 is configured to define an opening 3408.

The opening 3408 is configured to allow, in use, a flow of breathable pressurised gas to be delivered to the airway entrance of the patient from the vent chamber 3414. The opening 3408 is further configured to receive a flow of exhaled gas from the airway of the patient into the vent chamber 3414.

The vent body 3402 may be configured so that the opening 3408 fluidly connects in use to the seal-forming structure 3100, such that the breathable pressurised gas, and the exhaled gas, are able to pass through the opening 3408 of the vent body 3402 to/from the seal-forming structure 3100. For example, in forms of the technology in which the patient interface 3000 comprises a cushion module 3150 and the seal-forming structure 3100 is comprised as part of the cushion module 3150, the vent body 3402 is configured so that the opening 3408 fluidly connects to the cushion module 3150.

In the forms of the technology shown in FIGS. 8A, 8B and 8E to 8I, the vent body 3402 is configured so that the opening 3408 is located on the patient-facing surface 3450 of the vent body 3402 in use. The opening 3408 may also be located substantially in the centre of the patient-facing surface 3450 of the vent body 3402, i.e. so that, in use, part of the opening 3408 intersects with the mid-sagittal plane.

In the forms of the technology shown in FIGS. 8A, 8B and 8E to 8I, the opening 3408 is substantially rectangular in plan-view. However, in other forms the opening 3408 may be another shape, for example square, circular or oval. It will be understood that the shape of the opening 3408 may depend on the shape of the cushion module 3150 that fluidly connects to the opening 3408 in use. For example, the shape of the opening 3408 may be complementary to the part of the cushion module 3150 that connects to vent body 3402.

In certain forms of the technology, the opening 3408 of the vent body 3402 may be configured to fluidly connect to the cushion module 3150 by means of a threaded, friction-fit or snap-fit connection. The opening 3408 and/or the cushion module 3150 may be shaped and/or configured (for example may comprise additional components) to facilitate the means of connection. For example, they may comprise any one or more of the following: lugs; screw threads; depressions; O-rings; and seals.

5.3.4.4 Vent Holes

The vent body may be configured to define a plurality of vent holes 3410. In the forms of the present technology illustrated in FIGS. 8A to 8I, the non-patient-facing surface 3452 of the vent body 3402 is configured to include a plurality of vent holes 3410. In this form, the plurality of vent holes 3410 are located on an opposite side of the vent body to the opening 3408. The plurality of vent holes are configured to allow a vent flow of exhaled gas from the vent chamber to exit the vent assembly 3400 to ambient.

In certain forms of the vent assembly 3400, the plurality of vent holes 3410 may include, for example, about 20 to about 80 holes, or about 20 to about 50 holes, or about 25 to about 35 holes (for example, the form illustrated in FIGS. 8A to 8I has 28 holes). In certain forms, the plurality of vent holes 3410 are substantially circular in cross-section, although in other forms the vent holes 3410 may be shaped differently.

5.3.4.5 Valve

In one form of the present technology, the vent assembly 3400 comprises a valve 3412 constructed and arranged to allow the regulation of a vent flow of exhaled gas from the airway of a patient leaving the vent assembly to ambient.

As shown in FIGS. 8A, 8B and 8E to 8I, the valve 3412 in some forms may comprise parts contained within the vent chamber 3414 and part of the non-patient-facing surface 3452 of the vent body 3402. Alternatively, the valve may be separate to the surfaces of the vent body 3402 and may be connected to the interior of the vent chamber 3414 by an appropriate attachment mechanism.

As shown in the exemplary form of FIGS. 8A, 8B and 8E to 8I, the valve 3412 comprises two valve portions in a dual valve arrangement. The valve 3412 may comprise a first valve member 3420, a second valve member 3422, which comprise a first membrane 3424, a second membrane 3426, a first membrane mounting 3428, a second membrane mounting 3430, and the valve 3412 may further comprise a first seat portion 3432 and a second seat portion 3434. Each assembly of valve member, membrane, membrane mounting and seat portion forms one of the valve portions. The two valve portions may be substantially similar and arranged symmetrically in the vent assembly 3400. However, in alternative forms, the valve 3412 may consist of a single valve member, membrane, membrane mounting and seat portion.

In certain forms, for example as seen in FIGS. 8E to 8I, the valve 3412 may be configured such that a wall on the non-patient-facing side 3452 of the vent body 3402, i.e. a side opposite the vent opening 3408, is configured to include a first seat portion 3432 and a second seat portion 3434. The vent body 3402 may further comprise a wall between the first seat portion 3432 and the second seat portion 343, which may be referred to as a centre wall portion 3446.

In one form of the technology, the plurality of vent holes 3410 may be located in the centre wall portion 3446 of the valve 3412 and also in the first 3432 and second 3434 seat portions. In other forms, the plurality of vent holes 3410 may only be located in the first and second seat portions.

In one form of the technology the valve 3412 is configured to adopt a plurality of configurations, including a first configuration and a second configuration, where the valve at least partially blocks the plurality of vent holes by a different amount in each of the configurations, i.e. the vent holes are blocked by a different amount in the first configuration compared to the second configuration. The valve may also be configured to adopt a plurality of configurations between the first configuration and the second configuration, with the amount of blocking of the plurality of vent holes 3410 by the valve 3412 being different in each of the plurality of configurations. For the purposes of the ensuing description, the amount of blocking of the vent holes will be greater in the first configuration compared to the second configuration. The first configuration may therefore be referred to as the closed configuration and the second configuration may therefore be referred to as the open configuration. It will be understood that, unless the context requires otherwise, the terms "open" and "closed" refer to the relative amount of blocking and the valve 3412 may not be fully open or fully closed in either of the first or second configurations.

For the valve 3412 to adopt the different configurations, the first valve member 3420 and the second valve member 3422 may each be configured to adopt a number of positions, in each of which the degree to which the first membrane 3424 and the second membrane 3426 occlude a number of the plurality of vent holes 3410 varies. The first valve member 3420 and the second valve member 3422 may each be configured to move between a first position when the valve is in the first configuration and a second position when the valve is in the second configuration. When the valve 3412 is in the first, or closed, configuration, the first membrane 3424 and the second membrane 3426 may come into contact with at least a portion of the superior surface of the first 3432 and second 3434 seat portions respectively.

In some forms, in the closed configuration, the membranes fully occlude all, or a partial number of, the plurality of vent holes 3410 in the first and second seat portions, for example by adopting the contour of the superior surfaces of the seat portions. In other examples the vent holes 3410 that are occluded in the closed configuration of the first and second valve members 3420 and 3422 are partially occluded.

Typically, when the pressure of the air entering vent chamber 3414 is higher, as required by some patients for appropriate treatment, more air is forced to exit the vent holes to ambient such that, at higher treatment pressures, more air is typically lost by the system due to an increased vent flow rate. In one form of the present technology, the configuration adopted by the valve 3412 is based on the pressure of gas in the vent chamber 3414. A higher regulated air pressure entering the vent chamber 3414 will create more force on the valve members, urging them to fold inwards towards their closed positions, such that the vent holes 3410 are occluded to a greater extent, reducing what would otherwise have been an increased flow rate through the vent holes to ambient. A closed configuration of the valve 3412 when the pressure of air entering the vent chamber is relatively high is shown in FIG. 8F and FIG. 8H where the valve members 3420 and 3422 occlude some of the vent holes 3410. An open configuration of the valve 3412 when the pressure in the vent chamber is relatively low is shown in FIG. 8E and FIG. 8G where the valve members 3420 and 3422 do not occlude the vent holes 3410, or occlude the vent holes 3410 to a lesser extent than in the closed configuration.

The way in which the configuration of the valve 3412 varies with changes in pressure, and consequently the way in which the vent flow rate changes with pressure, may be predetermined based on certain characteristics of the valve 3412. Examples of such characteristics and how they may be varied will be discussed further below. In certain forms, the vent assembly 3400 may be configured so that, in use, the vent flow rate of exhaled air from the vent chamber 3414 through the vent holes 3410 to ambient is substantially constant for a range of pressures inside the vent chamber during inhalation.

Typically, the concentration of air received by a patient from a patient interface during inhalation can be affected by the amount of air lost to vent flow through the vent assembly during inhalation. In addition, the flush out of $CO_2$ during exhalation can be impeded by the arrangement of the vent. To address these effects, in one form of the present technology, the vent assembly 3400 is configured so that the configuration adopted by the valve 3412 is based on a breathing cycle of the patient in use, such that the configuration adopted by the valve when the patient exhales is different from the configuration adopted by the valve when the patient inhales.

In one form of the technology, the valve 3412 of the vent assembly 3400 may be configured to occlude a greater number of the plurality of vent holes 3410 during patient inhalation than during patient exhalation. This function serves to decrease vent flow through the plurality of vent holes 3410 to ambient during patient inhalation while conversely increasing vent flow through the plurality of vent holes 3410 to ambient during patient exhalation. This has the advantage of increasing the efficiency of air usage by both reducing the wastage of air delivered to the patient during inhalation (which may be pressurised and/or humidified) and increasing $CO_2$ flush out during exhalation. In turn, this may allow the use of a smaller humidifier 5000 and/or smaller RPT device 4000 than may otherwise be the case, or to reduce the power consumption of the humidifier 5000 and RPT device 4000 being used. In some forms, this may enable the use of a battery-powered and/or portable (e.g. head-mounted) RPT device 4000. Also, through the more efficient usage of air delivered from the RPT device 4000 and humidifier 5000, this may enable humidification and pressure rise times to be reduced. A further advantage of the present technology over conventional vents may include improved (e.g. more efficient) oxygen concentration.

The manner in which the configuration of the valve 3412 may vary between inhalation and exhalation will now be described. FIG. 8F and FIG. 8H show possible configurations of exemplary valves 3412 during patient inhalation. FIG. 8E and FIG. 8G show possible valve configurations during patient exhalation.

In the forms of the technology shown in FIG. 8F and FIG. 8H (which show the configuration of the valve 3412 during patient inhalation), air of a given pressure flows into the vent chamber 3414 of the vent assembly 3400 via the first inlet 3404 and the second inlet 3406 at each opposing side of the vent body 3402. The pressurised air then passes through the central vent opening 3408 and into the patient interface. As the pressurised air flows into the vent chamber 3414, the movement of air pushes against the interior-facing surfaces of the first valve member 3420 and the second valve member 3422, urging the valve members towards their closed configurations, i.e. causing the first valve member 3420 and the second valve member 3422 to fold inwards toward the centre of the vent chamber 3414. The action on the valve members of the air flow entering the vent chamber 3414 through the inlets may be in addition to the force on the valve members from the pressure of air in the vent chamber 3414, which may also tend to urge the valve members towards their closed configurations. As the valve members are urged closer to their closed configurations the vent holes 3410 are occluded to a greater extent. In the closed configuration, the first membrane 3424 and the second membrane 3426 come into contact with the first 3432 and second 3434 seat portions of the valve 3412 respectively, thus occluding the vent holes 3410, either fully (i.e. to the greatest extent for that particular valve configuration) or partially.

The action of the valve members at least partially occluding the plurality of vent holes 3412 during patient inhalation reduces the loss of air through the vent holes 3412 compared to if the vent holes 3412 were fully open, increasing the amount of air that passes out of the vent assembly 3400 through opening 3408 and that is received by the patient. In the case of full occlusion of all the vent holes 3412 by the valve members, all air loss through the vent holes 3412 is prevented.

In the forms of the technology shown in FIG. 8E and FIG. 8G (which show the configuration of the valve 3412 during patient exhalation), air is expelled by the patient, through the central vent opening 3408 and into the valve chamber 3414. As a result of hitting the wall on the far side of the valve chamber 3414 (e.g. the inner surface of centre wall portion 3446), exhaled air then flows laterally outwards toward each lateral side of the vent chamber 3414. This movement of air pushes against the first valve member 3420 and the second valve member 3422 and causes the first valve member 3420 and the second valve member 3422 to lift partially outwards away from their respective seat portions, thus reducing the amount of occlusion of the vent holes 3410. This increases the effective area of the vent holes 3410, allowing a relatively greater amount of exhaled air to flow through the vent holes 3410 to ambient compared to when the valve members occlude the vent holes 3410 to a greater degree. Thus, the vent flow rate through the plurality of vent holes 3410 to ambient is greater during exhalation when compared to during inhalation.

In some forms of the technology the first valve member 3420 and the second valve member 3422 may be positioned such that one end of the respective valve members is in the flow path of exhaled air from the patient, for example the valve members may be positioned proximate the opening 3408 of the vent assembly 3400. In the examples of the valve 3412 in FIGS. 8A to 8I, the ends of the valve members are, in their closed positions, adjacent the centre wall portion 3446. This means that exhaled air flowing out of the opening 3408 that impacts the centre wall portion 3446 (which is positioned opposite opening 3408) is pushed laterally outwards and into the ends of the valve members. This configuration may facilitate the movement of the valve members in response to air exhaled by a patient.

In some forms of the present technology, the valve 3412 may be configured to be biased to adopt the second configuration, wherein the amount of blocking of the plurality of vent holes by the valve is greater in the first configuration compared to the second configuration. The second configuration, in which the first valve member 3420 and the second valve member 3422 are biased towards, is an open configuration (see FIGS. 8E and 8G), i.e. the valve is biased not to be in the configuration in which the vent holes 3410 are occluded. The force of the movement of the air entering the vent chamber 3414 via the inlets, and/or the pressure of the air in the vent chamber 3414 causes the valve members to fold inwards, urging the valve members towards the first (closed) configuration (see FIGS. 8F and 8H). The bias serves to cause the valve 3412 to open as the pressure in the vent chamber 3414 reduces and/or as the patient exhales. This enables the valve 3412 to adopt different configurations, despite some force on the valve members existing that would urge them closed but for the bias, where that force is caused by the pressure in the vent chamber 3414 and/or the flow of air through the inlets. The degree of bias effects the position of the valve members (and therefore the degree of openness of the valve) for a given pressure of air in the vent chamber 3414 and, as will be explained later, the valve 3412 may be configured in a way that selects the degree of bias to achieve the desired characteristics of the vent assembly 3400.

FIG. 9A shows a graph 9010 showing vent flow rate versus supplied air pressure, for both exhalation and inhalation, for a patient interface 3000 similar to those shown in FIGS. 8A to 8I in accordance with one form of the present technology. In this form, the vent flow rate at a given pressure is different during inhalation compared with during exhalation. Also, the vent flow rate may change as the air pressure within the vent chamber 3414 is increased and the manner in which the vent flow rate changes with pressure is different for when the patient is exhaling compared to when the patient is inhaling. With some conventional vent assemblies, a higher air pressure within the system typically results in an increase in the vent flow rate, but with a vent assembly 3400 comprising a valve 3412 in accordance with certain forms of the present technology, the valve 3412 may be configured so that the pressure-flow characteristics differ. In the case of the vent assembly whose pressure-flow characteristics are shown in FIG. 9A, for example, a relatively constant vent flow rate is able to be maintained across a wide range of pressure levels for the configuration of the valve 3412 during inhalation. Furthermore, the valve 3412 is configured so that, in use, the vent flow rate of exhaled air from the vent chamber 3414 through the vent holes 3410 to ambient is substantially increased for a range of increased pressures inside the vent chamber during exhalation, which may be useful for achieving adequate $CO_2$ washout.

Forms of the technology in which the vent flow rate is relatively constant across a wide range of pressure levels may offer some advantages. In such forms it may be relatively simple to calculate the flow rate of air delivered to a patient's lungs at any pressure, for example. The air delivered to the patient's lungs is qual to the flow rate of air delivered to the patient interface 3000 by the RPT device 4000 minus the vent flow rate (assuming there are no leaks in the patient interface 3000). If the vent flow rate is constant, and known, this is easier to determine than if the vent flow rate changes with pressure. Furthermore, since the noise generated by the vent flow is affected by the vent flow rate, the noise generated by the vent assembly 3400 may be more constant at different pressures. In the case of bi-level therapy pressure systems, the RPT device 4000 delivers air at a higher pressure during inhalation compared to exhalation. In such a system, the cyclic noise variation may be less noticeable if the vent assembly 3400 is tuned to deliver a constant flow rate irrespective of the pressure.

5.3.4.5.1 Valve Members

In certain forms of the present technology, the valve 3412, as shown in FIGS. 8E to 8I, may be configured to consist of a first valve member 3420 and a second valve member 3422. The first valve member 3420 and the second valve member 3422 may comprise a first membrane 3424 and a second membrane 3426 respectively. The first valve member 3420 and the second valve member 3422 may also comprise a first membrane mounting 3428 and a second membrane mounting 3430 respectively. The first and second membranes may be separate components configured to attach to the first and second membrane mountings respectively. Alternatively, the first membrane 3424 may form a single unitary component with the first membrane mounting 3428 and the second membrane 3426 may form a single unitary component with the second membrane mounting 3430. The first and second membrane mountings are configured to mount the first and second valve members to the vent body 3402.

As has already been explained, in other forms of the technology the valve may comprise a single valve member. In such forms, the single valve member may comprise a membrane and membrane mounting.

In forms of the present technology, a function of each valve member is to move in response to air flow and/or air pressure within the vent chamber 3414. The movement of the valve member results in a variation in the degree of occlusion or exposure of a number of vent holes 3410, thus resulting in a change to the vent flow rate of air from the vent chamber to ambient through the vent holes 3410 based on the direction of air flow and level of air pressure within the vent chamber 3414. The first valve member 3420 and the second valve member 3422 may each be configured to adopt a number of configurations, in each of which the first membrane 3424 and the second membrane 3426 occlude the plurality of vent holes 3410 by a different degree. The first valve member 3420 and the second valve member 3422 may be configured to adopt a first position when the valve 3412 is in a first configuration, i.e. a closed configuration (as shown in FIGS. 8F and 8H) and to adopt a second position when the valve 3412 is in a second configuration, i.e. an open configuration (as shown in FIGS. 8E and 8G). The respective valve member/s at least partially block a subset of the plurality of vent holes by a different amount in the first position compared to the second position.

It will be understood that the plurality of configurations able to be adopted by the valve 3412 may be a continuous range of configurations. Equally, the valve members 3420 and 3422 may be configured to adopt a continuous range of positions.

As seen in FIGS. 8E to 8I, the first valve member 3420 and the second valve member 3422 may be configured to move such that, in the closed configuration, the first membrane 3424 and the second membrane 3426 may come into contact with the superior (i.e. inner) surface of the first 3432 and second 3434 seat portions respectively. In some forms, in the closed configuration, the membranes fully occlude all, or a subset of, the plurality of vent holes 3410 present in the first and second seat portions. In other examples the vent holes 3410 that are occluded in the closed configuration of the first and second valve members 3420 and 3422 are partially occluded, for example a stop may be provided to the upper surface of the seat portions that prevent the valve members fully occluding the vent holes when in the closed configuration.

In certain forms of the present technology, as shown in FIG. 8A and FIGS. 8E to 8I, the first valve member 3420 is positioned in a path of the first inlet flow of breathable gas from the first inlet 3404 and the second valve member 3422 is positioned in a path of the second inlet flow of breathable gas from the second inlet 3406. For example, the first valve member 3420 may be positioned such that the surface of the first valve member 3420 facing inwardly to the vent chamber 3414 (i.e. the upper surface in the orientation shown in FIGS. 8E to 8I) generally faces the first inlet 3404 so that the force of the flow of air against the surface urges the valve member 3420 towards the closed configuration, and likewise for the second valve member 3422.

As explained above, the first valve member 3420 comprises a first membrane 3424 mounted to the vent body 3402 and the second valve member 3422 comprises a second membrane 3426 mounted to the vent body by means of first membrane mounting 3428 and a second membrane mounting 3430 respectively.

The first membrane 3424 and the second membrane 3426 may be configured to be complementary to the shape of the first and second inlets or the vent body 3402. For example, if the inlet has a circular profile, the membrane may also be circular and of comparable size to the aperture of the inlet, in order to be able to fit within and move within the space defined by the vent body 3402. In other forms, the first and second membranes may be configured to fit and move within the vent chamber 3414 without being complementary in shape to the first and second inlets or vent body 3402.

In the forms of the technology shown in FIGS. 8E to 8I, the membrane mountings 3428 and 3430 are each mounted to an interior surface of the vent body 3402 at or proximate a respective side of the vent body 3402, for example at or proximate a part (e.g. an outer lateral end) of each seat portion, proximal to each inlet. Each membrane 3424 and 3426 (each of which is attached to one of the membrane mountings 3428 and 3430) extends from the respective membrane mounting generally inwardly within the vent body 3402 away from the nearby inlet. That is, each membrane may be mounted to the respective membrane mounting along a mounted edge and each membrane extends away from the mounted edge towards a free end of the membrane.

The first membrane 3424 and the second membrane 3426 may each be pivotally mounted to the vent body 3402 via the membrane mountings to allow the membranes to move in response to changes in air movement and air pressure.

The membranes and/or membrane mountings may be configured in such a manner that the valve members are biased towards the closed position so that the valve 3412 is biased to adopt the closed configuration, as explained above. For example, the way in which the membranes are mounted to the vent body 3402 may create the bias, or the manner in which the membranes are attached to the membrane mountings may create the bias. In certain forms, the membranes and membrane mountings are integrally formed in a manner in which the membranes tend to resiliently return to an open position in use.

In other forms the valve members 3420 and 3422 may each comprise a spring member configured to bias the valve members into an open position. For example, each spring member may act on the respective membrane to urge it into the open position, for example acting between the membrane and a wall of the valve chamber 3414.

In other forms, the shape of the valve members 3420 and 3422 may influence the bias of the valve members into the open position. For example, the thickness of the first and second membranes 3424 and 3426 may be configured to provide the desired level of bias. For another example, the membranes 3424 and 3426 may comprise a relatively thin region and a relatively thick region, with these regions configured and arranged to bias the valve members into the closed position and with the desired level of bias.

In certain forms, one or more edges of the valve membranes 3424 and 3426 may be rounded to promote smooth airflow around the membranes, thus reducing the potential noise generated by the system that may disturb patient and/or partner sleep.

In one form of the technology the first and second membranes 3424 and 3426 may be constructed from a soft, flexible material such as silicone. In some forms the membranes may have a degree of flexibility in order to bend inwardly and mould to the contour of the superior surface of the respective seat portion in the closed configuration. However, the membranes may also have a certain level of natural rigidity and/or resilience in order that the membrane is biased towards an open position and provides some degree of resistance to lower levels of air pressure in the vent chamber.

5.3.4.5.2 Active and Passive Vent Holes

In certain forms of the present technology, as seen in FIG. 8A and FIGS. 8E to 8I, the plurality of vent holes 3410 configured, in use, to allow a vent flow of exhaled gas from the vent chamber 3414 to exit the vent assembly 3400 to ambient, may be located in a wall of the vent body 3402 generally opposite the vent opening 3408, for example in the non-patient-facing side 3452 of the vent body 3402.

As shown most clearly in FIG. 8I, the plurality of vent holes 3410 may consist of one or more passive vent holes 3418 and/or one or more active vent holes 3416.

Passive vent holes 3418 are holes that retain the same level of occlusion irrespective of the configuration of the valve 3412. The vent assembly 3400 shown in FIGS. 8A to 8I is configured so that the amount of blocking of the one or more passive vent holes 3418 by the valve 3412 is the same when the valve is in the first configuration as when the valve member is in the second configuration. For example, the one or more passive vent holes 3418 are not blocked by the valve in the first configuration and are not blocked by the valve in the second configuration, i.e. the passive vent holes 3418 in the form of the technology shown in FIG. 8I are always open and un-occluded irrespective of the position of the valve members 3424 and 3426. In the form of the technology shown in FIGS. 8A to 8I the one or more passive vent holes 3418 are located in the centre wall portion 3446 of the vent body and the valve members 3424 and 3426 are not sufficiently large to cover the passive vent holes 3428 in their closed positions.

Active vent holes 3416 are holes whose level of occlusion varies depending on the configuration of the valve 3412, i.e. the active vent holes are either open (i.e. non-occluded or partially occluded) or closed (i.e. fully occluded) depending upon the position of the valve members. The vent assembly 3400 shown in FIGS. 8A to 8I is configured so that the valve 3412 at least partially blocks the one or more active vent holes 3416 by a different amount when the valve is in the first configuration compared to the second configuration.

In one form of the technology, the one or more active vent holes 3416 comprises a plurality of active vent holes which may be provided in both the first 3432 and second 3434 seat portions, while the one or more passive vent holes 3418 may be provided in the centre wall portion 3446 of the vent body 3402, between the first and second seat portions. The wall of the vent body in which the one or more passive vent holes are provided may be located directly opposite the opening 3408 of the vent body 3402. In other forms of the technology, the valve 3412 may only include the plurality of active vent holes 3416, located in both the first 3432 and second 3434 seat portions with no passive vent holes included. The plurality of vent holes 3410 are configured to allow a fluid connection between the air in the vent chamber 3414 and the ambient atmosphere outside of the vent assembly 3400, allowing exhaled air to pass as vent flow out of the vent chamber 3414 to ambient in use.

In certain forms the plurality of vent holes 3410 may be substantially circular in cross-section, although in other forms the vent holes 3410 may have another shape in cross-section, for example square, rectangular or oval.

In certain forms the vent holes 3410 may be further configured to pass through the full thickness of the centre wall portion 3446 and/or seat portions at an angle that is substantially perpendicularly to an inner surface of adjacent wall and/or seat portions. Alternatively, the vent holes may pass through the full thickness at an acute angle to the inner surface of an adjacent wall portion.

As seen in FIGS. 8E to 8I, the plurality of active vent holes 3416, located in both the first 3432 and second 3434 seat portions, may be occluded (fully or partially) when the first membrane 3424 and the second membrane 3426 come into contact with the superior surface of the first 3432 and second 3434 seat portions respectively. The location of the one or more passive vent holes 3418 (if included in the valve) is such that neither the first, nor the second membrane, is able to occlude any passive vent hole, irrespective of the membrane's position within the vent assembly 3400.

FIG. 9B shows a graph 9020 showing total vent flow rate 9022, as a sum of the vent flow rate 9024 for the passive vent holes 3418 and the vent flow rate 9026 for the active vent holes 3416, versus supplied air pressure for a patient interface 3000 in accordance with one form of the present technology. In this form, the vent flow rate 9024 through the one or more passive vent holes 3418 increases as the air pressure within the vent chamber 3414 increases, as is typical with vent holes that do not change in configuration. However, the vent flow rate 9026 through the plurality active vent holes 3416 decreases as the air pressure within the vent chamber 3414 increases as a result of the change in configuration of the valve 3412 as the pressure in the vent chamber 3414 changes. The total vent flow rate 9022, i.e. the sum of the vent flow rate of the passive vent holes 9024 and the vent flow rate of the active vent holes 9026, is constant as the air pressure within the vent chamber 3414 increases.

Configuring the valve 3412 to produce a total vent flow rate 9022 that does not increase as rapidly with pressure as would be the case if all the vent holes were passive, for example a total vent flow rate 9022 that remains substantially constant across a range of pressures may allow a smaller or less powerful RPT device 4000 to be used and may also result in more efficient humidification of the air received by the patient.

While the valve 3412 of the vent assembly 3400 that has the pressure-flow characteristics shown in FIG. 9B is configured in such a way so as to produce a total flow rate 9022 which remains substantially constant irrespective of the pressure, valves of other forms of the technology are configured in a way that produce a different pressure-flow characteristic. The valve 3412 may be configured in a way that produces the total vent flow rate 9022 by pressure that is particularly efficient for the patient interface 3000 to produce the desired treatment outcomes. Exemplary ways of altering the configuration of the valve 3412 to produce different characteristics will be described later.

5.3.4.5.3 Seat Portion

It has been explained that, in certain forms of the technology, the valve 3412 may include a first seat portion 3432 and a second seat portion 3434, and these may be connected by a centre wall portion 3446. In other forms, the valve 3412 may consist of a single seat portion.

The inner surface of a part of the wall of the vent body 3402 on the non-patient-facing side 3452 of the vent body 3402, i.e. the side opposite the vent opening 3408, may comprise the first seat portion 3432 and the second seat portion 3434. In certain forms of the technology, the first seat portion 3432 is proximate the first inlet 3404, the second seat portion 3434 is proximate the second inlet 3406 and the centre wall portion 3446 is directly opposite the vent opening 3408 of the vent assembly 3400.

In one form, as seen in FIG. 8E, the inner surface of the wall of the vent body 3402 on the non-patient-facing side 3452 may be configured in the form of a shallow, inverted U-shape such that the first seat portion 3432 and the second seat portion 3434 are generally oriented at an angle to the longitudinal axis of the vent body 3402 (which is oriented substantially perpendicular to the sagittal plane in use) and, in the form illustrated, are curved and substantially convex. The centre wall portion 3446 connecting the first and second seat portions may be curved or flat. The inverted U-shape configuration will henceforth be referred to as the convex surface valve.

However, the valve 3412 may take other configurations in alternative forms of the technology. For example, as in the form of the technology shown in FIGS. 8G and 8H, the valve 3412 may be configured so that the first seat portion 3432 and the second seat portion 3434 are substantially flat, wherein the first seat portion is oriented at an acute angle to the direction of the first inlet flow and the second seat portion is oriented at an acute angle to the direction of the second inlet flow. The centre wall portion 3446 may also be substantially flat. This configuration will henceforth be referred to as the flat surface valve.

In other forms of the technology, the valve 3412 may have other configurations. For example, the seat portions of the convex surface valve may have differing amounts of curvature in different forms. Additionally, or alternatively, the acute angle at which the first and second seat portions intersect with the centre wall portion 3446 of the flat surface valve (which may be equivalent to the angle that the seat portions form with the direction of the inlet flows in certain forms) may range from approximately zero to approximately ninety degrees in different forms of the technology.

In one form of the technology, when each of the first and second valve members 3420 and 3422 are in the first position, a surface of the respective membrane abuts against a respective seat portion. In this position, the respective membrane lies on the respective seat portion over the respective subset of the plurality of vent holes 3410 to block the respective subset of the plurality of vent holes. Thus, the first and second valve members 3420 and 3422 progressively occlude, or progressively uncover, a desired number of the plurality of vent holes 3410 for a given treatment air pressure at a given point in the patient's breathing cycle (such as during inhalation or during exhalation) depending on the bias of the first and second valve members. The convex surface valve configuration may permit the membranes to occlude or uncover the vent holes in a more progressive manner than the flat surface valve configuration.

In one form of the technology, the first membrane 3424 and the second membrane 3426 may adopt the shape of the contour of the inner surface of the first 3432 and second 3434 seat portions respectively (being either convex or flat), as the membranes come into contact with the seat portions. In other forms, the inner surface of each seat portion may be provided with spacers, or may alternatively be undulating, in order to prevent complete contact between the membrane and corresponding seat portion. In these forms, one or more of the vent holes 3410 may not be fully occluded when the valve 3412 is in the closed configuration.

In other forms of the technology, the first seat portion 3432 and the second seat portion 3434 may be configured so that, when each of the first and second valve members are in the first position, a free end of the first and second valve members 3420 and 3422 is spaced from the respective first and second seat portions to allow the flow of exhaled gas under the free ends of the first and second valve members. For example, the surface of each seat portion may be configured with an indentation, or a lip, so that the free end of the first and/or second membranes over-hang their respective seat portions. Alternatively, the free ends of the first and second membranes may be configured with a lip to assist the exhaled air in lifting the membranes away from the seat portions of the valve 3412. These forms may assist the membranes to lift off the seat portions, uncovering some of the plurality of vent holes 3410, as the patient exhales.

In certain forms of the technology, the centre wall portion 3446 may be curved, in either a convex or concave configuration, to deflect the air exhaled by the patient in a manner that facilitates the movement of the first and second membranes to adopt a desired position.

5.3.4.5.4 Tuning the Valve

It has already been explained that, as shown by way of example in FIGS. 9A and 9B, the vent flow rate of a vent assembly 3400 according to certain forms of the technology may depend on the pressure of the air within the vent chamber 3414. The manner in which the vent flow rate depends on the air pressure may be known as the pressure-flow relationship of the vent assembly 3400. The pressure-flow relationship for any vent assembly 3400 may be determined by certain aspects of the configuration of the valve 3412 of that vent assembly 3400. When designing or manufacturing a vent assembly 3400, any one or more of those aspects of the configuration may be selected in order to provide the desired pressure-flow relationship. The selection of these characteristics, and configuring the valve 3412 accordingly, may be referred to as tuning the valve. Tuning a valve 3412 enables the vent flow rate of the vent assembly 3400 comprising that valve 3412 for any given air pressure inside the vent chamber 3414 to be selected as desired.

As has already been explained, and is shown by way of example in FIG. 9A, the way in which the vent flow rate of a vent assembly 3400 according to certain forms of the technology varies with pressure may differ between inhalation and exhalation. Tuning the valve 3412 may involve configuring the valve 3412 to provide the desired pressure-flow relationship during inhalation and, separately, the desired pressure-flow relationship during exhalation.

The desired pressure-flow relationship may be determined based on various factors including, but not limited to: the nature of the patient interface 3000; the nature of the RPT device 4000; a patient's treatment preferences; a clinician's treatment preferences; and/or the nature of the respiratory treatment.

One factor that affects the vent flow rate at a given pressure, and therefore the overall pressure-flow relationship of the vent assembly 3400, is the degree that the vent holes 3410 are occluded at the given pressure. Two non-limiting examples of design characteristics that can affect the level of occlusion of the plurality of active vent holes 3416 at a given pressure include: the ratio between the effective vent opening area when the valve 3412 is closed compared to when it is open; and the resistance of the valve 3412 to opening, e.g. the resistance to opening of the first valve member 3420 and the second valve member 3422. Exemplary ways in which these characteristics may be varied in different forms of the technology will now be described. These design variants, as well as others not described herein, may be used separately or in any combination together.

It will be understood that the term "effective vent opening area" as used herein may refer to the effective area through which the vent flow may pass in order to escape the vent chamber 3414 to ambient. This area may be affected by the number, size and shape of the vent holes 3410 and also the degree to which the vent holes 3410 are occluded. For example, a high level of occlusion of the vent holes 3410 (e.g. by the valve members covering the vent holes to a greater extent) reduces the size of the opening through which the vent flow must pass through in order to reach the vent hole 3410, thus reducing the effective area of the vent.

The range of movement of the first valve member 3420 and second valve member 3422 between the open and closed configuration of the valve 3412 may be varied, for example the range of angles of the first membrane 3424 and the second membrane 3426 between their open and closed positions. The range through which the valve members can move between open and closed configurations affects the effective vent opening area in the fully open and fully closed configurations of the valve 3412, thus affecting the vent flow rate at the pressures at which the valve 3412 adopts these configurations.

The shapes of the seat portion(s) of the valve 3412 affect the way in which the effective vent opening area changes with a change in pressure in the vent chamber 3414. For example, in the forms of the technology shown in FIGS. 8A to 8I, the shape of the first seat portion 3432 and the second seat portion 3434, against which the first and second membranes respectively rest when fully closed. For example, in the form of the technology shown in FIGS. 8G and 8H, which has been referred to as the flat surface valve, the seat portions 3432 and 3434 have a generally flat surface facing toward the interior of the vent body 3402. In the exemplary form of the technology shown in FIGS. 8E and 8F, which has been referred to as the convex surface valve, the seat portions 3432 and 3434 have a generally convex-curved surface facing toward the interior of the vent body 3402. The form of the inner surface of the seat portions(s) affects the way in which the vent holes 3410 are occluded as pressure changes and the position of the valve members 3420 and 3422 change. Furthermore, the precise shape of the surfaces, e.g. the convex surface, can be selected to determine how the valve members close as the air pressure in the vent chamber 3414 increases.

In certain forms of the technology, the valve 3412 may comprise one or more stops to limit the extent that the valve members 3420 and 3422 occlude the vent holes 3410 in the fully closed configuration of the valve 3412. For example, the stops may comprise one or more spacers provided to the surface of the first seat portion 3432 and the second seat portion 3434 against which the valve members 3420 and 3422 abut. Additionally, or alternatively, the stops may comprise one or more spacers provided to the surface of the valve members 3420 and 3422 which abut against the first and second seat portions. Additionally, or alternatively, the surfaces of the seat portions and/or the valve members may be undulating or configured with a lip. These features may allow vent flow to flow through the vent holes 3410 even when the valve 3412 is in the fully closed configuration. The configuration of these features can be selected to determine the extent of occlusion of the valve 3412 in the closed configuration, which affects the pressure-flow relationship.

In other forms of the technology, the valve members 3420 and 3422 may comprise apertures so that vent flow may still flow through the vent holes 3410 even when the valve 3412 is in the fully closed configuration. For example, the membranes 3424 and 3426 may comprise apertures. The number, shape and/or size of these apertures may be selected to achieve the desired pressure-flow characteristics.

FIG. 9B illustrates how the total vent flow rate 9022 against pressure is made up of the sum of the vent flow rate 9024 for the passive vent holes and the vent flow rate 9026 for the active vent holes. Therefore, the overall pressure-flow characteristics of the vent assembly 3400 can be varied by altering the relative contributions of the passive vent flow rate 9024 and the active vent flow rate 9026 to the total vent flow rate 9022.

For example, the pressure-flow characteristics of a vent assembly 3400 according to certain forms of the technology may be affected by the relative size of the effective passive vent opening area compared to the effective active vent opening area. The relative size of these areas may be determined by, for example, the number of passive vent holes 3418 compared to the number of active vent holes 3416, the size of the passive vent holes 3418 compared to the active vent holes 3416, and/or the shape of the passive vent holes 3418 compared to the active vent holes 3416. For example, larger vent hole apertures and more numerous vent holes may result in a relatively higher vent flow rate.

It can be seen from the graph in FIG. 9B that, by configuring the valve 3412 to have a relatively greater contribution of the passive vent flow rate 9024 compared to the active vent flow rate 9026 (e.g. by having a greater total vent area of passive vent holes 3418 compared to active vent holes 3416), the total flow rate 9022 may generally more closely follow the pressure-flow characteristics of the passive vent holes 3418, e.g. the total flow rate 9022 may increase with an increase in pressure. Conversely, by configuring the valve 3412 to have a relatively greater contribution of the active vent flow rate 9026 compared to the passive vent flow rate 9024 (e.g. by having a greater total vent area of active vent holes 3416 compared to passive vent holes 3418), the total flow rate 9022 may generally more closely follow the pressure-flow characteristics of the active vent holes 3416, e.g. the total flow rate 9022 may decrease with an increase in pressure. In the example of the vent assembly 3400 which has the pressure-flow characteristics shown in FIG. 9B, the valve 3412 is configured so that the vent flow through the active vent holes 3416 and the vent flow through the passive vent holes 3418 sums to a similar vent flow rate, irrespective of the pressure, although individually the vent flow rate through the active vent holes and the flow rate through the passive vent holes changes with pressure. In another example, a valve 3412 may be configured with no passive vent holes 3418 (i.e. no vent holes that remain open even when the valve is in the closed configuration), in which case the total flow rate 9022 is made up solely of the active flow rate 9026.

It will be appreciated that the pressure-flow characteristics of the active vent holes 3416 may be varied by altering aspects of the configuration of the valve 3412, as described elsewhere in this specification.

Furthermore, in a vent assembly 3400 according to certain forms of the technology in which the configuration of the valve 3412 varies between an inhalation phase of the patient's breathing cycle compared to an exhalation phase, the contributions of the active vent flow rate 9026 and the passive vent flow rate 9024 to the total vent flow rate 9022 may differ between inhalation and exhalation phases, and the area of the active vent holes 3416 compared to the passive vent holes 3418 may be selected to provide the required pressure-flow characteristics for each phase. For example, a valve 3412 that is more responsive to the breathing cycle of the patient may comprise a greater area of active vents holes 3416 compared to passive vent holes 3418 (e.g. there may be more active vent holes 3416 compared to passive vent holes 3418).

The density of the vent holes 3410 (i.e. number of vent holes per unit area) in different regions of the vent body 3402 may alter the pressure-flow characteristics of the valve 3412 at different pressure levels. For example, in some forms of the technology, there may be a greater density of active vent holes 3416 at a location of the seat portions that is occluded at relatively low pressures compared to the density of active vent holes 3416 at a location of the seat portions that is not occluded at relatively low pressures. In other forms, there may be a lesser density of active vent holes 3416 in such a location. The characteristics of the valve 3412 at different pressure levels can be tuned by selecting the density of the vent holes 3410 in different regions accordingly.

It has already been described that the valve 3412 may be configured to be biased to adopt the open configuration. The amount of bias, e.g. the bias force, may affect the configuration adopted by the valve 3412 for a given pressure in the vent chamber 3414, which may affect the amount of occlusion of the vent holes 3410 and consequently the vent flow rate for the given pressure. Therefore, the valve 3412 may be configured with a selected amount of bias.

The bias acting on the valve 3412 may be selected by altering any one or more of a variety of factors. One such factor is the rigidity or flexibility of the first and second valve members 3420 and 3422, which affects their ease of movement when acted upon by the pressure of the air in the vent chamber 3414. The rigidity of the valve members may be affected by the material used to form the valve members and/or the thickness of that material and/or the shape of the valve members. For example, the type and/or thickness of the material used to form the first and second membranes 3424 and 3426 may affect the rigidity of the valve members.

The configuration of the first and second valve members may also impact their rigidity. For example, as has previously been described, the first and second valve members may comprise one or more apertures. The presence of apertures may alter the way in which the position of the valve members varies with air pressure in the vent chamber 3414. Furthermore, a spacing of the free end of the first and second valve members 3420 and 3422 from the respective first and second seat portions may alter the ease with which the first and second valve members are urged towards an open configuration by the action of air exhaled by the patient.

In another example, the use and nature (e.g. spring constant) of a spring member comprised as part of the valve members may alter the rigidity of the valve members and consequently their level of bias and/or resistance to movement to changes in air pressure.

A further discussion on characteristics of the valve 3412 which may affect the pressure-flow characteristics of the vent assembly 3400 will be understood upon reading the discussion in PCT Publication No. WO 02/051486 and US Patent Publication No. 2019/0209804, the contents of which are herein incorporated by reference.

5.3.4.6 Diffuser

The vent assembly 3400, as in FIG. 8B, may further comprise a diffuser 3436 to diffuse the vent flow of exhaled air from the vent chamber 3414 through the plurality of vent holes 3410 to ambient. A primary function of the diffuser may be to diffuse the vent flow, dispersing the exhaled gas. This prevents the exhaled air from "jetting" against the patient or their bed partner. A further function of the diffuser may be to reduce the amount of noise generated by the vent flow of air from the vent assembly 3400, preventing patient and/or partner sleep disturbance.

In one form of the technology, the diffuser 3436, as shown in FIG. 8D, may comprise a diffuser member 3440, a diffusing body 3438 (not shown), and one or more diffuser connectors 3442. The diffuser 3436 may be mounted to the vent body 3402 so that the diffuser member 3440 is positioned in the path of the vent flow of exhaled air through the plurality of vent holes and so that a surface of the diffuser member 3440, facing the vent body, is spaced apart from the vent body.

The one or more diffuser connectors 3442 may be configured to be received by one or more compatible vent body connectors 3444 located on the non-patient-facing exterior surface 3452 of the vent body 3402.

The diffuser member 3440 may be constructed from a plastics material.

The diffusing body 3438 may be positioned in a space between the vent body 3402 and the diffuser member 3440. The diffusing body 3438 may be a mesh type polyester material so as to absorb, diffuse, spread and disperse the vent flow of air from the vent chamber 3414.

The diffuser member 3440, which may serve as a cover to position and hold the diffusing body 3438 in place, may also act to deflect air exiting the vent holes 3410.

The diffuser 3436 may be shaped in a way that it complements the outer surface of the vent body 3402 it is located adjacent to. For example, in the form of the technology shown in FIGS. 8A to 8I, the vent body 3402 forms a recess on one side, e.g. the non-patient-facing surface 3452. The diffuser 3436 is shaped to fit into the recess so as to blend in within the overall form of the vent assembly 3400.

In the illustrated form of the technology, the diffuser member 3440 has a central wall portion 3448 and two wing portions 3449 connected at either end of the central wall portion 3448. The wing portions 3449 may be oriented at an angle, e.g. an acute angle, to the central wall portion 3448. In the illustrated example, the diffuser member 3440 has an angular U-shape in cross-section. The central wall portion 3448 and wing portions 3449 may be configured so that, when the diffuser 3436 is mounted to the vent body 3402, the central wall portion 3448 of the diffuser member 3440 is positioned generally parallel to, but perpendicularly spaced apart from, the centre wall portion 3446 of the vent body 3402, and the wing portions 3449 of the diffuser member 3440 are respectively positioned generally parallel to, but perpendicularly spaced apart from, one of the first seat portion 3432 and second seat portion 3434.

5.3.5 Connection Port

Connection port 3600 allows for connection of the patient interface 3000 to the air circuit 4170. In certain forms of the present technology, the patient interface 3000 may comprise a connection port 3600 located proximal a top, side or rear portion of a patient's head when the patient interface 3000 is worn during use. For example, in the forms of the present technology illustrated in FIGS. 7A and 7B, the connection port 3600 is located on top of the patient's head. At least two gas delivery tubes 3350, which are comprised as part of the positioning and stabilising structure 3300, receive the flow of breathable gas from the connection port 3600 and deliver the flow of breathable gas to the airway entrance of the patient via the plenum chamber 3200. Forms of the technology with a patient interface with a connection port 3600 positioned proximate the top of the patient's head in use may make it easier or more comfortable for a patient to lie or sleep in certain positions compared to forms in which the connection port 3600 is located in front of the patient's face.

5.3.6 Forehead Support

In one form, the patient interface 3000 includes a forehead support 3700.

In other forms, the patient interface 3000 does not include a forehead support. Advantageously, the exemplary patient interface 3000 shown in FIG. 7A comprises a positioning and stabilising structure 3300 that is able to hold the seal-forming structure 3100 in sealing position without connection to a forehead support or any frame or strap members that lie in front of the patient's face at or around eye level.

5.3.7 Anti-Asphyxia Valve

In one form, the patient interface 3000 includes an anti-asphyxia valve 6200.

An anti-asphyxia valve (AAV) 6200 provides a mechanism to enable the patient 1000 to breathe in situations where the blower 4142 stops providing a flow of pressurised air. In certain forms, the AAV 6200 comprises an opening which forms an airflow path between the patient 1000 and the ambient air to provide the patient 1000 with a supply of fresh air. This reduces the risk of excessive $CO_2$ rebreathing by a patient.

In the forms of the technology illustrated in FIGS. 8A to 8I, the first valve member 3420 and the second valve member 3422 of the vent assembly 3400 are biased to an open configuration, otherwise referred to as the second configuration (as shown in FIGS. 8E and 8G), such that a number of vent holes 3410 (both active vent holes 3416 and passive vent holes 3418 if present) are un-occluded in the absence of pressurised air entering the vent chamber 3414 through the first 3404 and second 3406 inlets.

5.3.8 Ports

In one form of the present technology, a patient interface 3000 includes one or more ports that allow access to the volume within the plenum chamber 3200. In one form this allows a clinician to supply supplemental oxygen. In one form, this allows for the direct measurement of a property of gases within the plenum chamber 3200, such as the pressure. The pressure in the plenum chamber 3200 may be measured using a pressure sensor.

5.3.9 Pressure Sensor

In certain forms of the technology the patient interface 3000 may comprise a pressure sensor to measure the pressure of gas in a volume inside the patient interface 3000, for example inside the plenum chamber 3200. In some forms, the pressure sensor may be in communication with the therapy device controller 4240, which may be configured to control the pressure generator 4140 to alter the rate of the air supply for delivery to the patient's airways based on the pressure detected by the pressure sensor. The pressure detected by the pressure sensor may be indicative of inhalation and/or exhalation of the patient.

5.4 RPT Device

An RPT device 4000 in accordance with one aspect of the present technology comprises mechanical, pneumatic, and/or electrical components and is configured to execute one or more algorithms 4300. The RPT device 4000 may be configured to generate a flow of air for delivery to a patient's airways, such as to treat one or more of the respiratory conditions described elsewhere in the present document.

In one form, the RPT device 4000 is constructed and arranged to be capable of delivering a flow of air in a range of −20 L/min to +150 L/min while maintaining a positive pressure of at least 4 $cmH_2O$, or at least 10$cmH_2O$, or at least 20 $cmH_2O$.

The RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator 4140 capable of supplying air at positive pressure (e.g., a blower 4142), an outlet muffler 4124 and one or more transducers 4270, such as pressure sensors 4272 and flow rate sensors 4274.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

5.4.1 Pressure Generator

In one form of the present technology, a pressure generator 4140 for producing a flow, or a supply, of air at positive pressure is a controllable blower 4142. For example the blower 4142 may include a brushless DC motor 4144 with one or more impellers housed in a volute. The blower may be capable of delivering a supply of air, for example at a rate of up to about 120 litres/minute, at a positive pressure in a range from about 4 $cmH_2O$ to about 20 $cmH_2O$, or in other forms up to about 30 $cmH_2O$. The blower may be as described in any one of the following patents or patent applications the contents of which are incorporated herein by reference in their entirety: U.S. Pat. Nos. 7,866,944; 8,638,014; 8,636,479; and PCT Patent Application Publication No. WO 2013/020167.

The pressure generator 4140 may be under the control of the therapy device controller 4240. The therapy device controller 4240 may be configured to control the pressure generator 4140 to alter the rate of the air supply for delivery to the patient's airways as a result of a stimulus external to the RPT device 4000, for example based on a pressure detected in the patient interface 3000, which may be indicative of inhalation and/or exhalation of the patient.

In other forms, a pressure generator 4140 may be a piston-driven pump, a pressure regulator connected to a high pressure source (e.g. compressed air reservoir), or a bellows.

5.5 Air Circuit

An air circuit 4170 in accordance with an aspect of the present technology is a conduit or a tube constructed and arranged to allow, in use, a flow of air to travel between two components such as RPT device 4000 and the patient interface 3000.

In particular, the air circuit 4170 may be in fluid connection with the outlet of the pneumatic block 4020 and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller 4230. One example of an air circuit 4170 comprising a heated wire circuit is described in U.S. Pat. No. 8,733,349, which is incorporated herewithin in its entirety by reference.

5.5.1 Oxygen Delivery

In one form of the present technology, supplemental oxygen 4180 is delivered to one or more points in the pneumatic path, such as upstream of the pneumatic block 4020, to the air circuit 4170 and/or to the patient interface 3000.

5.6 Humifier

In one form of the present technology there is provided a humidifier 5000 (e.g. as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 5A and FIG. 5B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

5.7 Glossary

For the purposes of the present technology disclosure, in certain forms of the present technology, one or more of the following definitions may apply. In other forms of the present technology, alternative definitions may apply.

5.7.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

In the example of patient respiration, a flow rate may be nominally positive for the inspiratory portion of a breathing cycle of a patient, and hence negative for the expiratory portion of the breathing cycle of a patient. Total flow rate, Qt, is the flow rate of air leaving the RPT device. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Patient: A person, whether or not they are suffering from a respiratory condition.

Pressure: Force per unit area. Pressure may be expressed in a range of units, including $cmH_2O$, $g\text{-}f/cm_2$ and hectopascal. 1 $cmH_2O$ is equal to 1 $g\text{-}f/cm_2$ and is approximately 0.98 hectopascal. In this specification, unless otherwise stated, pressure is given in units of $cmH_2O$.

The pressure in the patient interface is given the symbol Pm, while the treatment pressure, which represents a target value to be achieved by the mask pressure Pm at the current instant of time, is given the symbol Pt.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

5.7.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a thermoplastic polymer of Bisphenol-A Carbonate.

5.7.1.2 Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

'Soft' materials may include silicone or thermo-plastic elastomer (TPE), and may, e.g. readily deform under finger pressure.

'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions.

Floppy structure or component. A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 $cmH_2O$ pressure.

As an example, an I-beam may comprise a different bending stiffness (resistance to a bending load) in a first direction in comparison to a second, orthogonal direction. In another example, a structure or component may be floppy in a first direction and rigid in a second direction.

5.7.2 Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): The work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:

(i) Flattened: Having a rise followed by a relatively flat portion, followed by a fall.

(ii) M-shaped: Having two local peaks, one at the leading edge, and one at the trailing edge, and a relatively flat portion between the two peaks.

(iii) Chair-shaped: Having a single local peak, the peak being at the leading edge, followed by a relatively flat portion.

(iv) Reverse-chair shaped: Having a relatively flat portion followed by single local peak, the peak being at the trailing edge.

Hypopnea: According to some definitions, a hypopnea is taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:

(i) a 30% reduction in patient breathing for at least 10 seconds plus an associated 4% desaturation; or (ii) a reduction in patient breathing (but less than 50%) for at least 10 seconds, with an associated desaturation of at least 3% or an arousal.

Hyperpnea: An increase in flow to a level higher than normal.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow rate during the inspiratory portion of the respiratory flow waveform.

Respiratory flow rate, patient airflow rate, respiratory airflow rate (Qr): These terms may be understood to refer to the RPT device's estimate of respiratory flow rate, as opposed to "true respiratory flow rate" or "true respiratory flow rate", which is the actual respiratory flow rate experienced by the patient, usually expressed in litres per minute.

Tidal volume (Vt): The volume of air inhaled or exhaled during normal breathing, when extra effort is not applied.

(inhalation) Time (Ti): The duration of the inspiratory portion of the respiratory flow rate waveform.

(exhalation) Time (Te): The duration of the expiratory portion of the respiratory flow rate waveform.

(total) Time (Ttot): The total duration between the start of one inspiratory portion of a respiratory flow rate waveform and the start of the following inspiratory portion of the respiratory flow rate waveform.

Typical recent ventilation: The value of ventilation around which recent values of ventilation Vent over some predetermined timescale tend to cluster, that is, a measure of the central tendency of the recent values of ventilation.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

5.7.3 Ventilation

Adaptive Servo-Ventilator (ASV): A servo-ventilator that has a changeable, rather than fixed target ventilation. The changeable target ventilation may be learned from some characteristic of the patient, for example, a respiratory characteristic of the patient.

Backup rate: A parameter of a ventilator that establishes the minimum breathing rate (typically in number of breaths per minute) that the ventilator will deliver to the patient, if not triggered by spontaneous respiratory effort.

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

Expiratory positive airway pressure (EPAP): a base pressure, to which a pressure varying within the breath is added to produce the desired mask pressure which the ventilator will attempt to achieve at a given time.

End expiratory pressure (EEP): Desired mask pressure which the ventilator will attempt to achieve at the end of the expiratory portion of the breath. If the pressure waveform template $\Pi(\Phi)$ is zero-valued at the end of expiration, i.e. $\Pi(\Phi)=0$ when $\Phi=1$, the EEP is equal to the EPAP.

Inspiratory positive airway pressure (IPAP): Maximum desired mask pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the base pressure (e.g., PS=IPAP−EPAP). In some contexts pressure support means the difference which the ventilator aims to achieve, rather than what it actually achieves.

Servo-ventilator: A ventilator that measures patient ventilation, has a target ventilation, and which adjusts the level of pressure support to bring the patient ventilation towards the target ventilation.

Spontaneous/Timed (S/T): A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator delivers a breath of air to a spontaneously breathing patient, it is said to be triggered to do so at the initiation of the respiratory portion of the breathing cycle by the patient's efforts.

Typical recent ventilation: The typical recent ventilation Vtyp is the value around which recent measures of ventilation over some predetermined timescale tend to cluster. For example, a measure of the central tendency of the measures of ventilation over recent history may be a suitable value of a typical recent ventilation.

5.7.4 Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g. about 360 degrees. In certain forms an elbow may be removable from a mating component, e.g. via a snap connection. In certain forms, an elbow may be assembled to a mating component via a one-time snap during manufacture, but not removable by a patient.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

Edge of a surface: A boundary or limit of a surface or region.

Path: In certain forms of the present technology, 'path' will be taken to mean a path in the mathematical-topological sense, e.g. a continuous space curve from f(0) to f(1) on a surface. In certain forms of the present technology, a 'path' may be described as a route or course, including e.g. a set of points on a surface. (The path for the imaginary person is where they walk on the surface, and is analogous to a garden path).

Path length: In certain forms of the present technology, 'path length' will be taken to mean the distance along the surface from f(0) to f(1), that is, the distance along the path on the surface. There may be more than one path between two points on a surface and such paths may have different path lengths. (The path length for the imaginary person would be the distance they have to walk on the surface along the path).

5.7.4.1 Holes

Figure 1A:
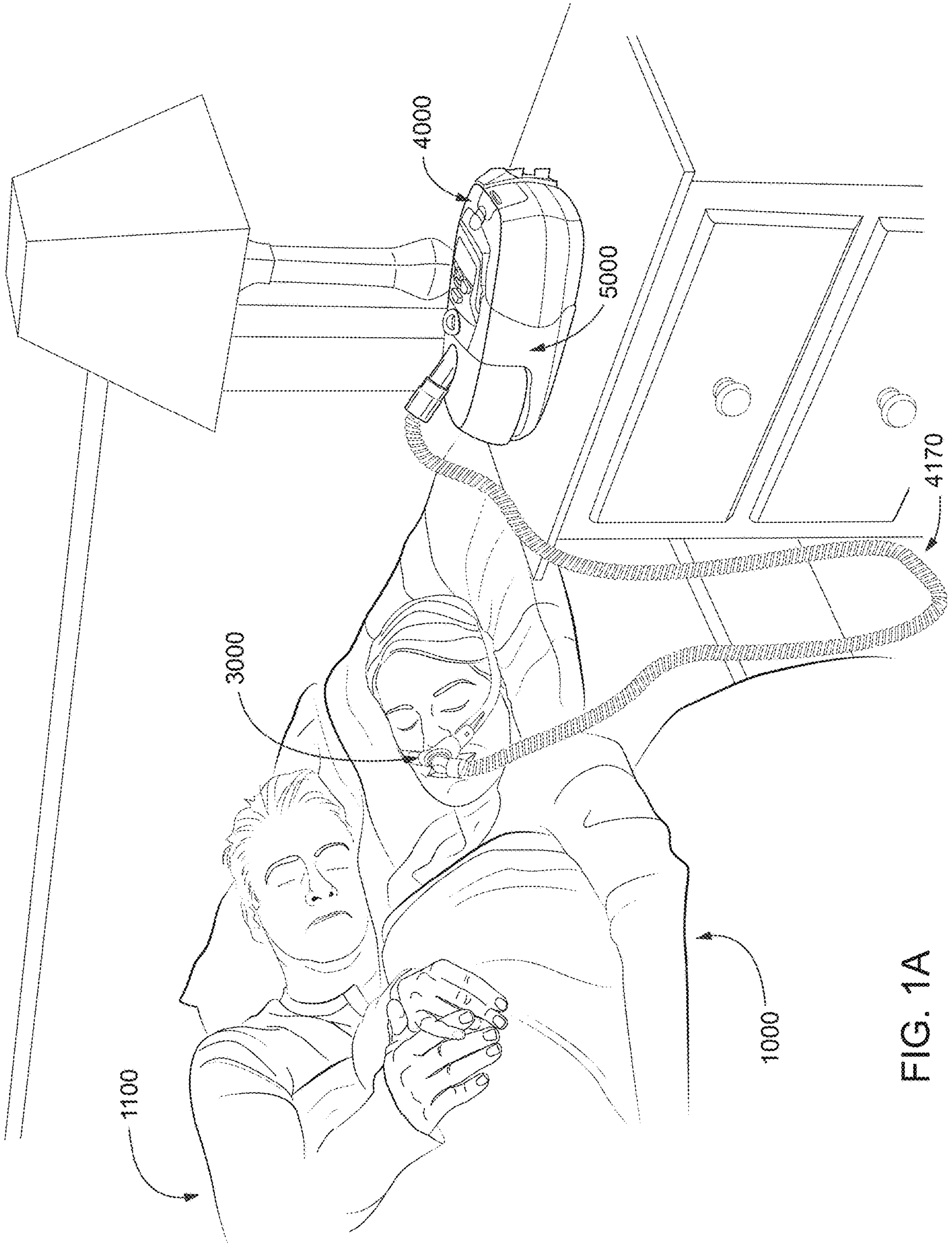
Figure 2A:
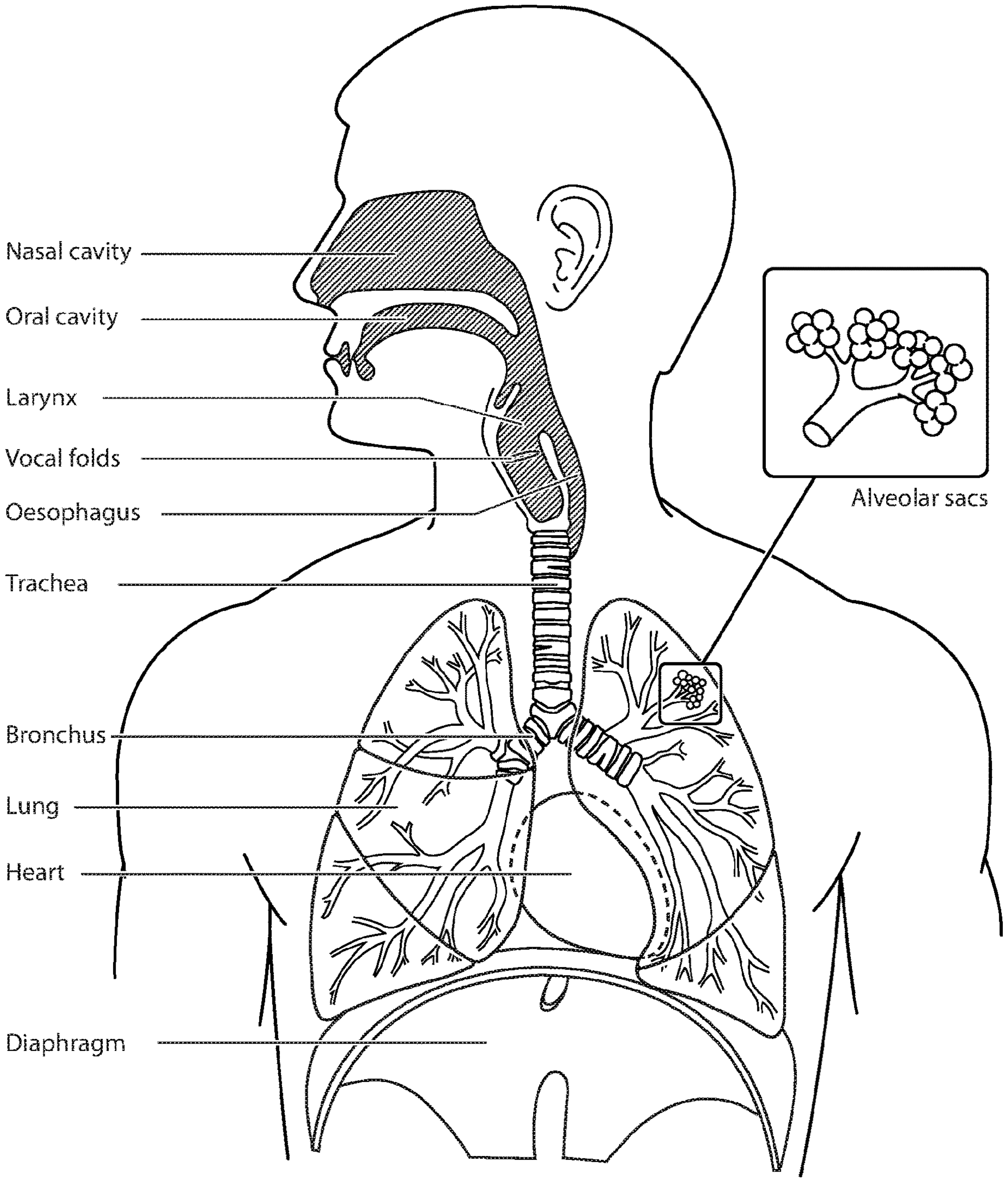
Figure 3A:
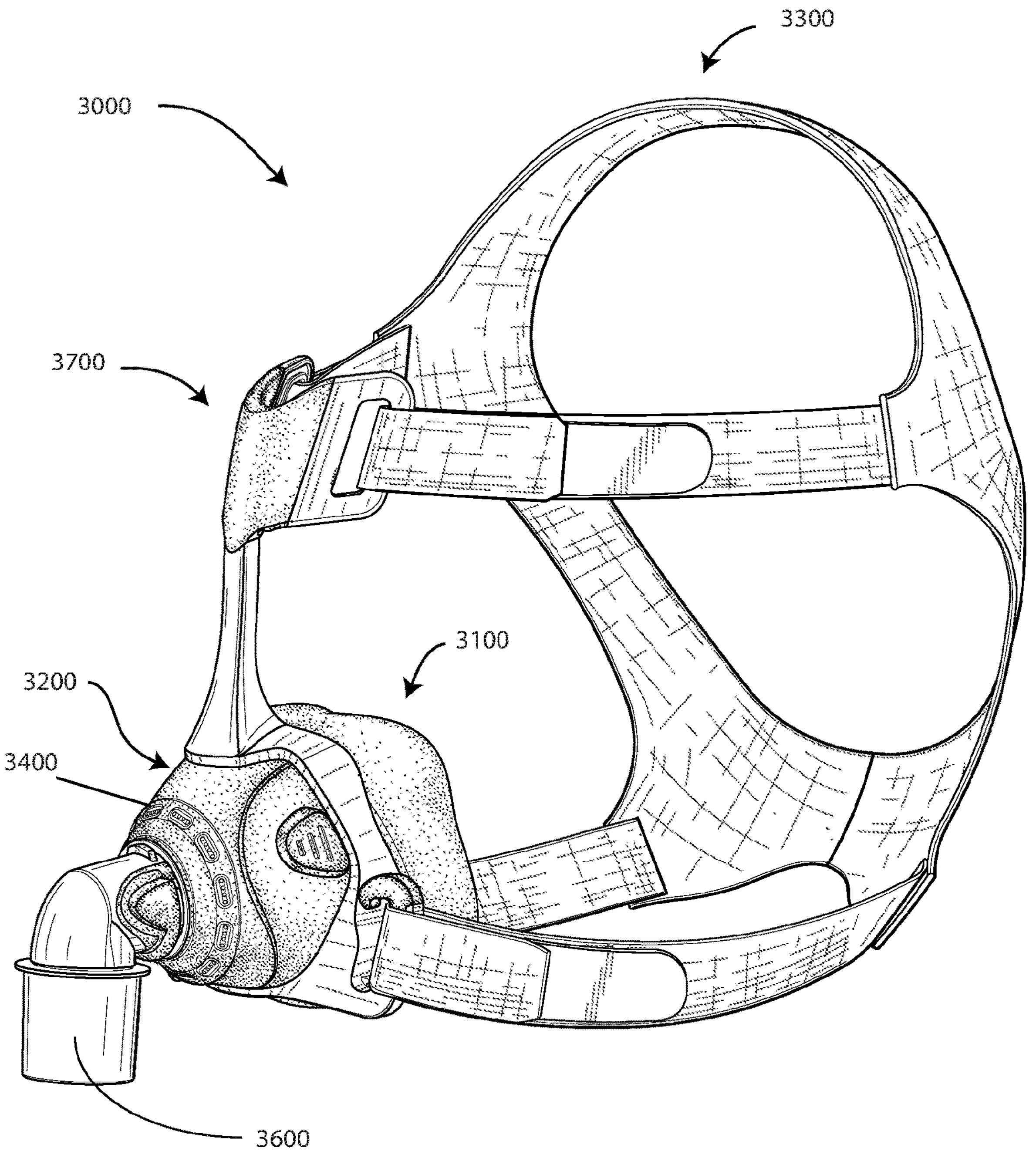
Figure 4A:
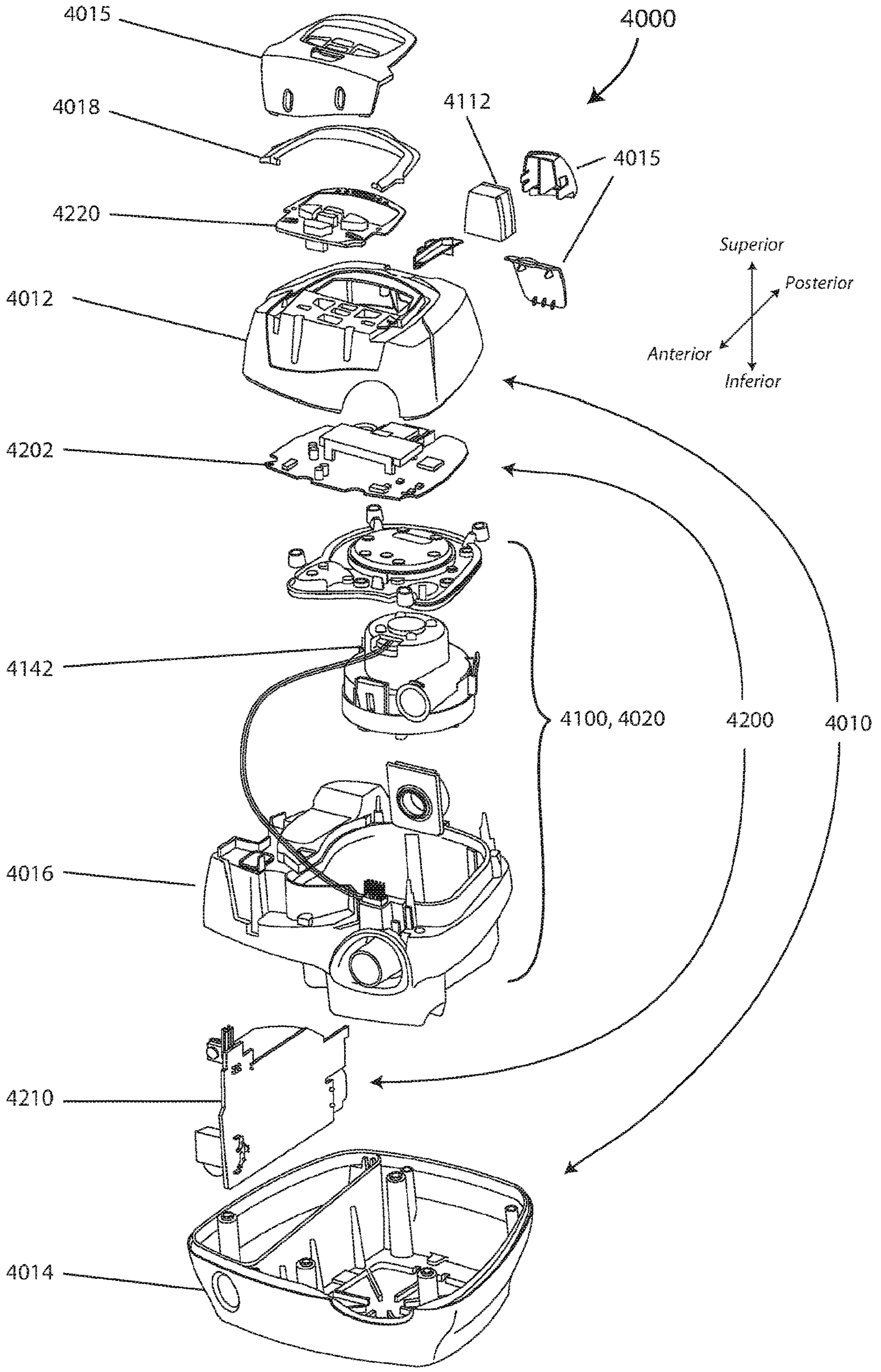
FIG. 4A shows an RPT device in accordance with one form of the present technology.
Figure 4B:
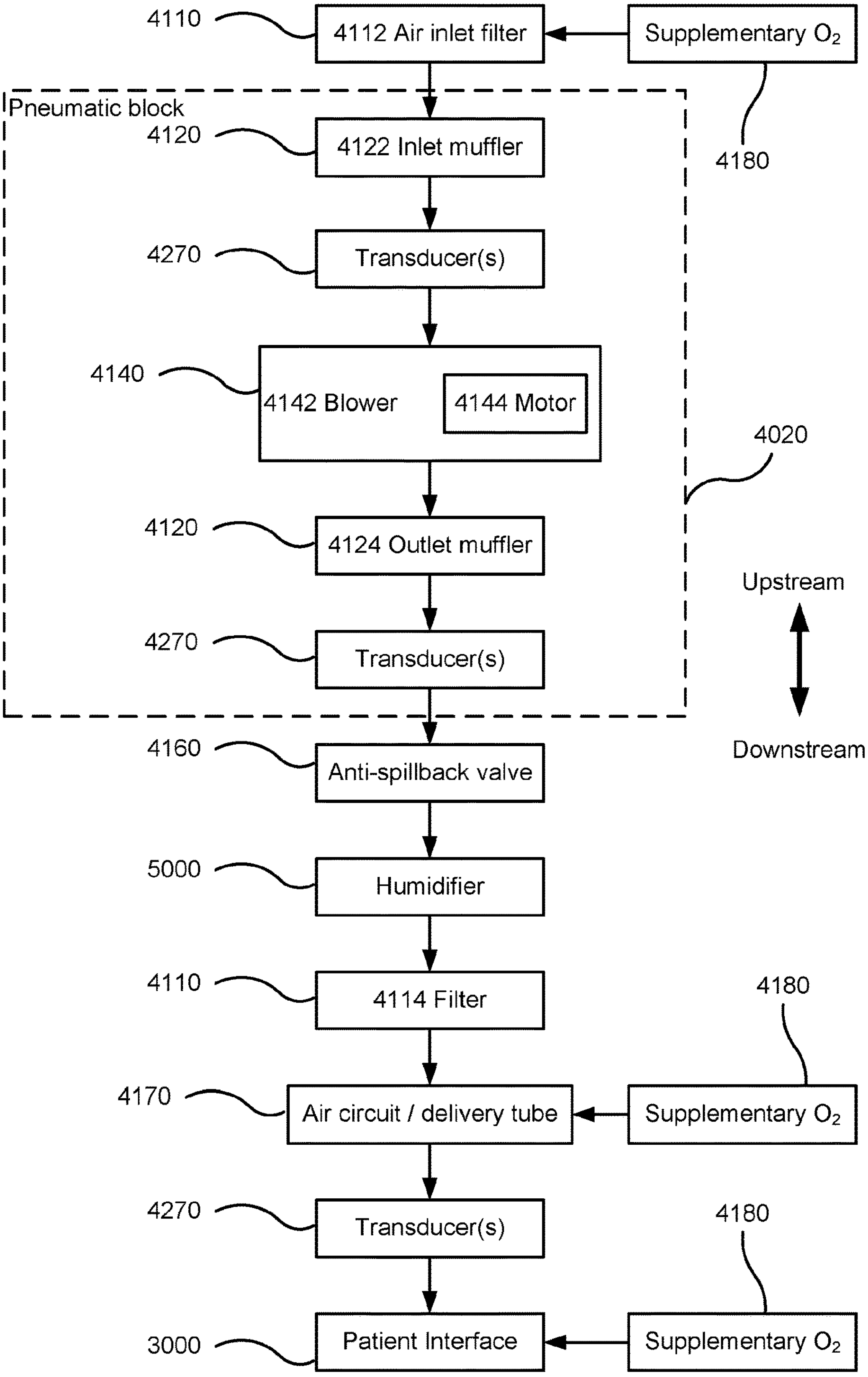
FIG. 4B is a schematic diagram of the pneumatic path of an RPT device in accordance with one form of the present technology. The directions of upstream and downstream are indicated.

A surface may have a one-dimensional hole, e.g. a hole bounded by a plane curve or by a space curve. Thin structures (e.g. a membrane) with a hole, may be described as having a one-dimensional hole. See for example the one dimensional hole in the surface of structure shown in FIG. 3I, bounded by a plane curve.

A structure may have a two-dimensional hole, e.g. a hole bounded by a surface. For example, an inflatable tyre has a two dimensional hole bounded by the interior surface of the tyre. In another example, a bladder with a cavity for air or gel could have a two-dimensional hole. See for example the cushion of FIG. 3L and the example cross-sections therethrough in FIG. 3M and FIG. 3N, with the interior surface bounding a two dimensional hole indicated. In a yet another example, a conduit may comprise a one-dimension hole (e.g. at its entrance or at its exit), and a two-dimension hole bounded by the inside surface of the conduit. See also the two dimensional hole through the structure shown in FIG. 3K, bounded by a surface as shown.

5.8 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

5.9

| REFERENCE SIGNS LIST | |
|---|---|
| patient | 1000 |
| bed partner | 1100 |
| patient interface | 3000 |
| seal forming structure | 3100 |
| cushion module | 3150 |
| plenum chamber | 3200 |
| positioning and stabilising structure | 3300 |
| superior tube portion | 3304 |
| first end | 3305 |
| second end | 3306 |
| strap | 3310 |
| tab | 3320 |
| gas delivery tube | 3350 |
| rail portion | 3362 |
| sleeve | 3363 |
| sleeves | 3364 |
| vent assembly | 3400 |
| vent body | 3402 |
| first inlet | 3404 |
| second inlet | 3406 |
| opening | 3408 |
| vent holes | 3410 |
| valve | 3412 |
| vent chamber | 3414 |
| active vent holes | 3416 |
| passive vent holes | 3418 |
| first valve member | 3420 |
| second valve member | 3422 |
| first membrane | 3424 |
| second membrane | 3426 |
| first membrane mounting | 3428 |
| second membrane mounting | 3430 |
| first seat portion | 3432 |
| second seat portion | 3434 |
| diffuser | 3436 |
| diffusing body | 3438 |
| diffuser member | 3440 |
| diffuser connectors | 3442 |
| vent body connectors | 3444 |
| centre wall portion | 3446 |
| central wall portion | 3448 |
| wing portion | 3449 |
| patient-facing surface | 3450 |
| non-patient facing surface | 3452 |
| first side | 3454 |
| second side | 3456 |
| connection port | 3600 |
| elbow | 3610 |
| forehead support | 3700 |

-continued

| REFERENCE SIGNS LIST | |
|---|---|
| RPT device | 4000 |
| external housing | 4010 |
| upper portion | 4012 |
| lower portion | 4014 |
| panels | 4015 |
| chassis | 4016 |
| handle | 4018 |
| pneumatic block | 4020 |
| pneumatic components | 4100 |
| air filter | 4110 |
| inlet air filter | 4112 |
| muffler | 4120 |
| inlet muffler | 4122 |
| outlet muffler | 4124 |
| pressure generator | 4140 |
| blower | 4142 |
| DC motor | 4144 |
| anti-spill back valve | 4160 |
| air circuit | 4170 |
| supplemental oxygen | 4180 |
| electrical components | 4200 |
| Printed circuit board assembly (PCBA) | 4202 |
| electrical power supply | 4210 |
| input devices | 4220 |
| transducers | 4270 |
| humidifier | 5000 |
| humidifier inlet | 5002 |
| humidifier outlet | 5004 |
| humidifier base | 5006 |
| humidifier reservoir | 5110 |
| conductive portion | 5120 |
| humidifier reservoir dock | 5130 |
| locking lever | 5135 |
| water level indicator | 5150 |
| heating element | 5240 |
| graph | 9010 |
| graph | 9020 |
| total vent flow rate | 9022 |
| passive vent flow rate | 9024 |
| active vent flow rate | 9026 |

The invention claimed is:

1. A vent assembly for a patient interface for delivering a flow of breathable gas at a positive pressure to an airway entrance of a patient, the vent assembly comprising:

a vent body at least in part defining a vent chamber configured to contain gas at the positive pressure, the vent body being configured to define:

a first inlet on a first side of the vent body, the first inlet being configured to receive a first inlet flow of breathable gas into the vent chamber;

a second inlet on a second side of the vent body, the second side being opposite the first side, the second inlet being configured to receive a second inlet flow of breathable gas into the vent chamber;

an opening configured to allow exit of the flow of breathable gas from the vent chamber for delivery to the airway entrance and to receive a flow of exhaled gas from the patient into the vent chamber; and a plurality of vent holes configured to allow a vent flow of exhaled gas from the vent chamber to ambient, wherein the plurality of vent holes comprises;

a plurality of active vent holes formed in a respective seat portion of a first seat portion and a second seat portion of the vent body, and one or more passive vent holes;

wherein the vent assembly further comprises a valve configured to adopt a first configuration and a second configuration, wherein the valve at least partially blocks the plurality of active vent holes by a different amount in the first configuration compared to the second configuration, and wherein the valve is configured so that the configuration adopted by the valve is based on the positive pressure of gas in the vent chamber.

2. A vent assembly as claimed in claim 1, wherein the valve is configured to adopt a plurality of configurations between the first configuration and the second configuration, wherein the amount of blocking of the plurality of active vent holes by the valve is different in each of the plurality of configurations.

3. A vent assembly as claimed in claim 1, wherein the configuration adopted by the valve is based on a breathing cycle of the patient in use.

4. A vent assembly as claimed in claim 3, wherein the configuration adopted by the valve when the patient exhales is different from the configuration adopted by the valve when the patient inhales.

5. A vent assembly as claimed in claim 1, wherein the valve is configured to be biased to adopt the second configuration, wherein the amount of blocking of the plurality of active vent holes by the valve is greater in the first configuration compared to the second configuration.

6. A vent assembly as claimed in claim 1, wherein the vent assembly is configured so that the amount of blocking of the one or more passive vent holes by the valve is the same when the valve is in the first configuration as when the valve member is in the second configuration.

7. A vent assembly as claimed in claim 6, wherein the vent assembly is configured so that the one or more passive vent holes are not blocked by the valve in the first configuration and are not blocked by the valve in the second configuration.

8. A vent assembly as claimed in claim 1, wherein the valve comprises a first valve member and a second valve member, wherein each of the first valve member and the second valve member is configured to adopt a first position when the valve is in the first configuration and to adopt a second position when the valve is in the second configuration, wherein the each of the first and second valve members at least partially blocks a subset of the plurality of active vent holes by a different amount in the first position compared to the second position.

9. A vent assembly as claimed in claim 8, wherein the first valve member is positioned in a path of the first inlet flow of breathable gas from the first inlet and the second valve member is positioned in a path of the second inlet flow of breathable gas from the second inlet.

10. A vent assembly as claimed in claim 8, wherein the first valve member comprises a first membrane mounted to the vent body and the second valve member comprises a second membrane mounted to the vent body.

11. A vent assembly as claimed in claim 10, wherein the first membrane and the second membrane are pivotally mounted to the vent body.

12. A vent assembly as claimed in claim 10, wherein, when each of the first and second valve members are in the first position, a surface of the first and second membrane abuts against a respective seat portion of a first seat portion and a second seat portion of the vent body.

13. A vent assembly as claimed in claim 12, wherein, when each of the first and second valve members are in the first position, the first and second membrane lies on the respective seat portion over the first and second subset of the plurality of active vent holes to block the first and second subset of the plurality of active vent holes.

14. A vent assembly as claimed in claim 12, wherein a mounted edge of the first membrane is pivotally mounted to the vent body at or proximate a part of the first seat portion proximal to the first inlet and the first membrane extends from the mounted edge away from the first inlet, and wherein a mounted edge of the second membrane is pivotally mounted to the vent body at or proximate a part of the second seat portion proximal to the second inlet and the second membrane extends from the mounted edge away from the second inlet.

15. A vent assembly as claimed in claim 12, wherein the first seat portion and the second seat portion are configured so that, when each of the first and second valve members are in the first position, a free end of the first and second valve members is spaced from the respective first and second seat portion to allow the flow of exhaled gas under the free ends of the first and second valve members.

16. A vent assembly as claimed in claim 12, wherein the first seat portion and the second seat portion are substantially flat.

17. A vent assembly as claimed in claim 12, wherein the first seat portion and the second seat portion are substantially convex.

18. A vent assembly as claimed in claim 12, wherein the first seat portion is oriented at an acute angle to the direction of the first inlet flow and the second seat portion is oriented at an acute angle to the direction of the second inlet flow.

19. A vent assembly as claimed in claim 1, wherein the vent assembly is configured with the plurality of vent holes on an opposite side of the vent body to the opening.

20. A vent assembly as claimed in claim 12 wherein the one or more passive vent holes are provided in a wall of the vent body between the first and second seat portions.

21. A vent assembly as claimed in claim 20, wherein a wall of the vent body in which the one or more passive vent holes are provided is positioned directly opposite the opening.

22. A vent assembly as claimed in claim 1, wherein the vent assembly is configured so that, in use, a vent flow rate of the flow of exhaled air from the vent chamber through the plurality of vent holes to ambient is substantially constant for a range of pressures inside the vent chamber.

23. A vent assembly as claimed in claim 1, wherein the vent assembly further comprises a diffuser to diffuse the vent flow of exhaled gas from the vent chamber to ambient.

24. A vent assembly as claimed in claim 23, wherein the diffuser comprises a diffuser member mounted to the vent body so that the diffuser member is positioned in the path of the vent flow of exhaled gas through the plurality of vent holes and so that a surface of the diffuser member facing the vent body is spaced apart from the vent body.

25. A vent assembly as claimed in claim 24, wherein the diffuser comprises a diffusing body positioned in a space between the vent body and the diffuser member.

26. A patient interface for delivering a flow of breathable gas at a positive pressure to an airway entrance of a patient, the patient interface comprising:

a vent assembly as claimed in claim 1;

a plenum chamber pressurisable to a therapeutic pressure of at least 4 $cmH_2O$ above ambient air pressure, the plenum chamber comprising the vent body of the vent assembly;

a seal-forming structure constructed and arranged to form a seal with a region of the patient's face surrounding the airway entrance, said seal-forming structure having a hole therein such that the flow of breathable gas at said therapeutic pressure is delivered to the airway entrance, the seal-forming structure constructed and arranged to maintain said therapeutic pressure in the plenum chamber throughout the patient's respiratory cycle in use; and a positioning and stabilising structure to provide a force to hold the seal-forming structure in a therapeutically effective position on the patient's head, the positioning and stabilising structure comprising:

at least two gas delivery tubes to receive the flow of breathable gas from a connection port configured to be positioned on top of the patient's head in use and to deliver the flow of breathable gas to the airway entrance via the plenum chamber, the at least two gas delivery tubes being constructed and arranged to contact, in use, at least a region of the patient's head superior to an otobasion superior of the patient's head and the at least two gas delivery tubes being constructed and arranged so that, in use, at least one of the at least two gas delivery tubes is positioned in use on each side of the patient's head and configured to extend across a respective cheek region, wherein one of the at least two gas delivery tubes fluidly connects to the first inlet of the vent assembly and another of the at least two gas delivery tubes fluidly connects to the second inlet of the vent assembly.

27. A patient interface as claimed in claim 26, wherein the positioning and stabilising structure comprises a bendable strap.

28. A patient interface as claimed in claim 26, wherein the seal-forming structure is configured to seal around an inferior periphery of the nose.

* * * * *